(12) United States Patent
Gerdts et al.

(10) Patent No.: US 6,946,448 B2
(45) Date of Patent: Sep. 20, 2005

(54) IN UTERO ORAL NUCLEIC ACID IMMUNIZATION

(75) Inventors: Volker Gerdts, Saskatoon (CA); Lorne Babiuk, Saskatoon (CA); Sylvia van Drunen Littel-van den Hurk, Saskatoon (CA); Philip J. Griebel, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 236 days.

(21) Appl. No.: 10/155,867

(22) Filed: May 23, 2002

(65) Prior Publication Data

US 2003/0086905 A1 May 8, 2003

Related U.S. Application Data

(63) Continuation-in-part of application No. 09/927,408, filed on Aug. 10, 2001, now abandoned.
(60) Provisional application No. 60/224,737, filed on Aug. 10, 2000.

(51) Int. Cl.$^7$ .................. A01N 43/04; A01N 63/00; A61K 48/00; A61K 39/29; A61K 39/245
(52) U.S. Cl. .................. 514/44; 424/227.1; 424/228.1; 424/229.1; 424/230.1; 424/231.1; 424/93.2
(58) Field of Search .................. 514/44; 424/227.1, 424/228.1, 229.1, 230.1, 231.1, 450

(56) References Cited

PUBLICATIONS

Butts, et al., "DNA immunization of infants: potential and limitations," Vaccine,16:1444–1449,(1998).

Gerdts, et al., "Fetal Immunization by a DNA Vaccine Delivered Into the Oral Cavity," Nature Med., 6:929–932, (2000).

Gerdts, et al., "Oral DNA Vaccination In Utero Induces Mucosal Immunity and Immune Memory in the Neonate," J. Immunol.,168:1877–1885,(2002).

Le Potier, et al., "Study of the delivery of the gD gene of pseudorabies virus to one–day–old piglets by adenovirus or plasmid DNA as ways to by–pass the inhibition of immune response by colostral antibodies," Vet. Microbiol 55:75–80(1997).

McCluskie and Davis, "Novel Strategies Using DNA for the Induction of Mucosal Immunity," Crit. Rev. Immunol., 19:303–329, (1999).

Sekhon and Larson, "In utero gene transfer into the pulmonary epithelium," Nature Med.,1:(11),1201–1203 (1995).

Van Drunen Littel–van den Hurk, et al., "Immunization of Neonates with DNA Encoding a Bovine Herpesvirus Glycoprotein Is Effective in the Presence of Maternal Antibodies," Viral Immunology, 12:67–77,(1999).

Watts, et al. "Fetal immunization of baboons induces a fetal–specific antibody response," Nature Med., 5:427–430 (1999).

Denis et al., "Vaccination with Plasmid DNA Encoding Mycobacterial Antigen 85A Stimulates a $CD4^+$ and $CD8^+$ T–Cell Epitopic Repertoire Broader Than That Stimulated by Mycobacterium Tuberculosis H37Rv Infection," Infection and Immunity, 66(4):1527–1533 (1998).

Fu et al., "Dose Dependence of CTL Precursor Frequency Induced by a DNA Vaccine and Correlation with Protective Immunity Against Influenza Virus Challenge," The Journal of Immunology, 162:4163–4170 (1999).

Letvin et al., "Potent, Protective Anti–HIV Immune Responses Generated by Bimodal HIV Envelope DNA Plus Protein Vaccination," Proc. Natl. Acad. Sci. USA, 94:9378–9383 (1997).

Primary Examiner—Deborah Crouch
(74) Attorney, Agent, or Firm—Robins & Pasternak LLP

(57) ABSTRACT

Methods of nucleic acid immunization comprising the in utero delivery of nucleic acid molecules that encode one or more selected antigens to a vertebrate fetus are disclosed.

12 Claims, 10 Drawing Sheets

IN UTERO ORAL NUCLEIC ACID IMMUNIZATION

CROSS-REFERENCE TO RELATED APPLICATION

This application is a continuation-in-part of U.S. application Ser. No. 09/927,408, filed Aug. 10, 2001 now abandoned, from which application priority is claimed under 35 USC §120, which claims the benefit of provisional patent application Ser. No. 60/224,737, filed Aug. 10, 2000, from which priority is claimed under 35 USC §119(e)(1), and which applications are incorporated herein by reference in their entireties.

TECHNICAL FIELD

The present invention relates generally to methods of nucleic acid immunization. In particular, the present invention pertains to methods of achieving immune responses by the in utero delivery of nucleic acid molecules that encode one or more selected antigens.

BACKGROUND

Infectious diseases are the primary cause of neonatal morbidity and mortality in humans. The World Health Organization has estimated that in 1995 approximately 8 million (6.4% of live-born) infants died within the first year of life from these diseases, including 5 million during the first week of life. Some of the important pathogens involved include Herpes simplex virus (HSV), Human Immunodeficiency Virus (HIV), Hepatitis B virus (HBV), Human Cytomegalovirus (HCMV), Group B *Streptococcus* (GBS), *Haemophilus* and *Chlamydia* (Wright, et al., *Vaccine* (1998) 16:1355–1359; Mulholland, K., *Vaccine* (1998) 16:1360–1362). Infection with these pathogens can occur in utero, following early rupture of the aminiotic membranes or during birth. In addition, infection may be transmitted during labor by non-sterile techniques, by breast feeding or during the first days of life in a perinatal nursery. To reduce the risk of disease transmission, caesarian sections, prophylactic treatment with antibiotics or maternal antiviral therapy during the last trimester are used where available, together with improved neonatal care. None of these approaches, however, completely eliminates the risk of neonatal infection.

Since the first reports in 1993 (Ulmer, et al., *Science* (1993) 259:1745–1749), numerous studies have demonstrated that vaccination with DNA represents a very useful tool to induce immunity in people and animals (Donelly, et al., *Annu Rev Immunol.* (1997) 15:617–648; Babiuk, et al., *Adv. Vet. Med.* (1999) 41:163–179. In addition to the simplicity of production and delivery, DNA vaccines possess the advantages of attenuated live vaccines with respect to their immunogenicity, and a level of biological safety similar to inactivated vaccines. DNA vaccines represent, therefore, a significant advance in vaccinology. Most studies with DNA vaccines have been performed in mature animals, but within the last three years, several studies have reported succesful immunization of newborns of a variety of species (Butts, et al., *Vaccine* (1998) 16:1444–1449). As a result, DNA vaccines for rabies, hepatitis B, lymphocytic choriomeningitis-, influenza-, measles-, sendai-, porcine-, bovine herpesvirus-1, and tetanus toxoid are in development (Butts, et al., supra; Le Potier, et al., *Vet. Microbiol* (1997) 55:75–80; Van Drunen Littel-van den Hurk, et al., *Viral Immunology* (1999) 12:67–77). These approaches are designed, however, to prevent infections during the first weeks of life. In contrast, fetal immunization might prevent infection in utero, during birth and in the immediate postnatal period and may, therefore, have a significant impact on neonatal survival and the quality of life of infants.

A major factor for preventing an initial infection of the infant is the induction of effective mucosal immunity. This is of particular importance since the majority of infectious agents enter the host via the mucosal surfaces (Staats, et al., In *Mucosal Vaccines,* 1996 (Kiyono, H., et al., eds.) pp. 17–39). Newborns face an especially high risk of vertical disease transmission during birth and by breast feeding. Recent studies have shown that DNA vaccination via the mucosal surfaces can induce both mucosal and systemic immunity (McCluskie and Davis, *Crit. Rev. Immunol.* (1999) 19:303–329).

Watts, et al., *Nature Med.* (1999) 5:427–430 immunized fetal baboons against hepatitis B three times during the last trimester with 5 μg of the recombinant hepatitis B surface antigen protein. Antigen-specific serum antibodies were detectable within 10 days after the second immunization in 75% (5/8) of the immunized fetuses. However, induction of a cell-mediated immune response was not evaluated. Sekhon and Larson, (*Nature. Med.* (1995) 11:1201–1203) demonstrated that introduction of adenoviral vectors into the amniotic fluid resulted in transgene expression in lung tissue of fetal rats.

The development of effective fetal immunization protocols would provide a valuable approach to reducing the high risk of diseases in newborn children.

SUMMARY OF THE INVENTION

The present invention is based on the discovery that a single immunization with a nucleic acid vaccine, delivered orally to a fetus through the amniotic fluid, induces high serum antibody titers and cell-mediated immune responses in immunized fetuses, as well as in the newborn subjects. Moreover, this route of delivery provides direct access to a number of potential mucosal sites in the upper and lower respiratory tract, induces local immunity in the oral cavity and does not induce immune tolerance. In utero nucleic acid immunization, therefore, provides an efficient means of limiting vertical transmission of infectious diseases before, during and after birth.

Accordingly, in one embodiment, the present invention provides a method of delivering a recombinant vector encoding a selected antigen to a fetal vertebrate subject in utero to elicit an immune response. The method comprises administering the recombinant vector orally via the amniotic fluid to the fetus, under conditions that permit the expression of the antigen, thereby eliciting an immunological response to the antigen.

In preferred embodiments, the vertebrate subject is a mammal. Additionally, the recombinant vector may be a nonviral vector.

In additional embodiments, the invention is directed to a method of eliciting an immune response in a vertebrate subject. The method comprises administering a first vaccine composition comprising a nucleic acid molecule encoding a selected antigen to a fetal vertebrate subject in utero, mucosally via the amniotic fluid, under conditions that permit the expression of the antigen, thereby eliciting an immunological response to the antigen.

In certain embodiments, the nucleic acid molecule is included in a recombinant vector. Moreover, the administering may be by nonviral-mediated delivery, the vertebrate subject may be a mammal and the antigen may be a viral antigen.

In another embodiment, the invention is directed to a method of eliciting an immune response in a vertebrate subject, wherein the method comprises administering a first vaccine composition comprising a recombinant vector encoding a selected antigen to a fetal vertebrate subject in utero, orally, via the amniotic fluid, under conditions that permit the expression of the antigen, thereby eliciting an immunological response to the antigen, wherein the administering is nonviral-mediated delivery.

In certain embodiments of the above-described methods, the viral antigen is a herpesvirus or hepatitis virus antigen. Moreover, delivery is done in the third trimester.

In additional embodiments, the invention further comprises administering a second vaccine composition to the vertebrate subject at birth to boost the immune response to the antigen encoded by the nucleic acid molecule in the first vaccine composition. The second vaccine composition may include the nucleic acid molecule present in the first vaccine composition. Alternatively, the second vaccine composition may be a subunit vaccine composition that includes the antigen encoded by the nucleic acid molecule present in the first vaccine composition.

In yet a further embodiment, the invention is directed to a method of eliciting an immune response in a mammalian subject. The method comprises:

(a) administering a first vaccine composition comprising a recombinant vector encoding a selected viral antigen to a fetal mammalian subject in utero during the third trimester, orally via the amniotic fluid, under conditions that permit the expression of the antigen and elicit an immunological response to the antigen; and (b) administering a second vaccine composition to the mammalian subject at birth to boost the immune response to the antigen encoded by the recombinant vector in the first vaccine composition.

In certain embodiments, the second vaccine composition comprises the recombinant vector present in the first vaccine composition. In other embodiments, the second vaccine composition is a subunit vaccine composition that comprises the antigen encoded by the recombinant vector present in the first vaccine composition.

In yet other embodiments, the administering in step (a) and/or step (b) is nonviral-mediated delivery.

These and other embodiments of the subject invention will readily occur to those of skill in the art in view of the disclosure herein.

BRIEF DESCRIPTION OF THE FIGURES

FIG. 1 shows lymphoproliferative responses of fetal blood mononuclear cells (PBMC) and retropharyngeal lymph node cells.

FIG. 5A shows gD-specific serum antibody responses. Differences in antibody titres were statistically significant between DNA-immunized and PBS-treated lambs at birth (**$p<0.001$) and following secondary immunization between DNA/DNA and both PBS/PBS and PBS/DNA groups (+$p<0.01$) and between the DNA/PBS and the PBS/PBS group (*$p<0.05$). FIG. 5B shows gD-specific LPR of blood mononuclear cells. Iin utero DNA-immunized lambs had significantly increased LPR in comparison to PBS-treated lambs at birth (**$p<0.01$; *$p<0.05$). Following secondary immunization, the LPR of the DNA/DNA group was significantly (**$p<0.01$; *$p<0.05$) increased in comparison to all other treatment groups.

Figure 8:
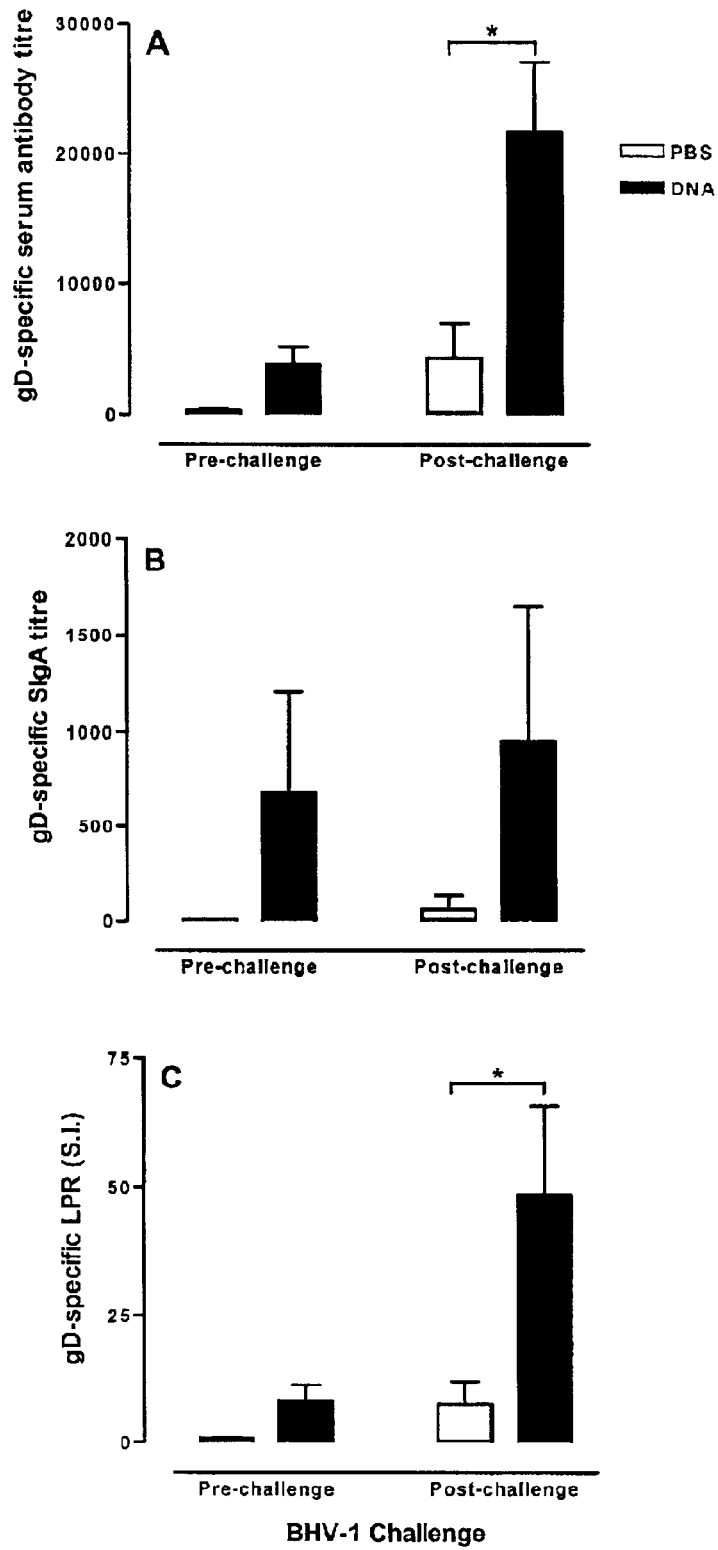
FIGS. 8A, 8B and 8C show induction of both systemic and mucosal immune responses following in utero immunization. Fetal lambs were orally immunized in utero with either 500 $\mu$g pSLIA-tgD plasmid (DNA; n=5) or PBS (PBS; n=4). Between 7–10 days of age, newborn lambs were aerosol-challenged with $5-7 \times 10^7$ infectious particles of BHV-1 strain 108. gD-specific serum antibody titres (FIG.

8A), SIgA-titres in nasal secretions (FIG. 8B), and LPR in blood lymphocytes (FIG. 8C) were assayed at the day of challenge (pre-challenge) and 12 days after challenge with BHV-1 (post-challenge). *p<0.01.

Figure 9:
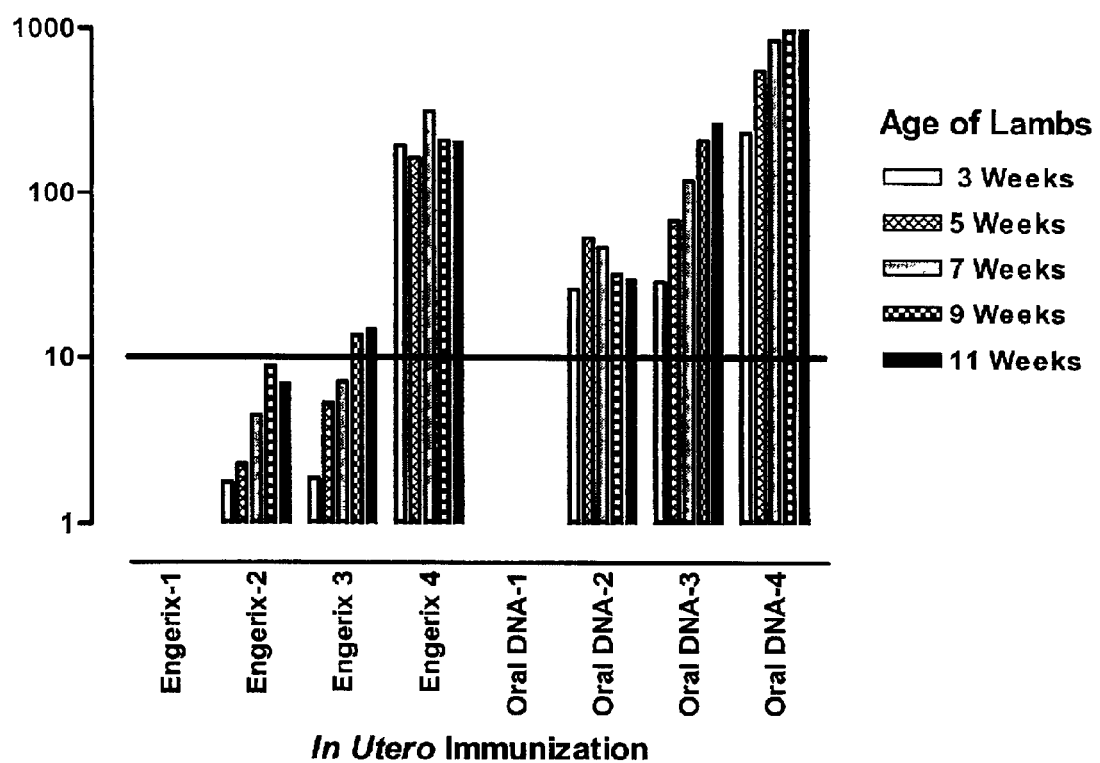

FIG. 9 shows induction of protective HB serum antibody titres following oral DNA immunization in utero. Fetal lambs were orally immunized in utero with 500 μg pMCG-16HBsAg plasmid (DNA; n=4) or injected intramuscularly with 10 μg of recombinant HBsAg (Engerix; n=4). Serum samples were collected bi-weekly for the first 3 months after birth. HBsAg-specific serum antibody titres (mIU/ml) were determined with a commercial Microparticle Enzyme Immunoassay and protective antibody titres (>10 mIU/ml) are indicated by the horizontal line on graph.

DETAILED DESCRIPTION

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook, Fritsch & Maniatis, *Molecular Cloning: A Laboratory Manual*, Vols. I, II and III, Second Edition (1989); Perbal, B., *A Practical Guide to Molecular Cloning* (1984); the series, *Methods In Enzymology* (S. Colowick and N. Kaplan eds., Academic Press, Inc.); and *Handbook of Experimental Immunology*, Vols. I–IV (D. M. Weir and C. C. Blackwell eds., 1986, Blackwell Scientific Publications).

All publications, patents and patent applications cited herein, whether supra or infra, are hereby incorporated by reference in their entirety.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

A. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

By "isolated" when referring to a nucleotide sequence, is meant that the indicated molecule is present in the substantial absence of other biological macromolecules of the same type. Thus, an "isolated" nucleic acid molecule which encodes a particular polypeptide refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

The terms "polypeptide" and "protein" are used interchangeably herein and refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

The terms "analog" and "mutein" refer to biologically active derivatives of the reference molecule, or fragments of such derivatives, that retain desired activity, such as immunological activity as described herein. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to peptides having one or more peptide mimics ("peptoids"), such as those described in International Publ. No. WO 91/04282. Preferably, the analog or mutein has at least the same immunoactivity as the native molecule. Methods for making polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5–10 conservative or non-conservative amino acid substitutions, or even up to about 15–25 conservative or non-conservative amino acid substitutions, or any integer between 5–25, so long as the desired function of the molecule remains intact. One of skill in the art may readily determine regions of the molecule of interest that can tolerate change by reference to Hopp/Woods and Kyte-Doolittle plots, well known in the art.

By "antigen" is meant a molecule which contains one or more epitopes that will stimulate a host's immune system to make a cellular antigen-specific immune response when the antigen is produced, or a humoral antibody response. For purposes of the present invention, antigens can be derived from any of several known viruses, bacteria, parasites and fungi. Furthermore, for purposes of the present invention, an "antigen" refers to a protein which includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts which produce the antigens.

By "fragment" is intended a polypeptide or polynucleotide consisting of only a part of the intact full-length polypeptide sequence and structure. An "immunogenic fragment" of a particular protein will generally include at least about 5–10 contiguous amino acid residues of the full-length molecule, preferably at least about 15–25 contiguous amino acid residues of the full-length molecule, and most preferably at least about 20–50 or more contiguous amino acid residues of the full-length molecule, that define an epitope, or any integer between 5 amino acids and the full-length sequence, provided that the fragment in question retains the ability to elicit an immune response as defined below. A polynucleotide encoding such a fragment will include the requisite number of bases.

The term "epitope" as used herein refers to a sequence of at least about 3 to 5, preferably about 5 to 10 or 15, and not more than about 1,000 amino acids (or any integer therebetween), which define a sequence that by itself or as part of a larger sequence, will stimulate a host's immune system to make a cellular antigen-specific immune response when the antigen is presented, or a humoral antibody response. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998–4002; Geysen et al. (1986) *Molec. Immunol.* 23:709–715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824–3828 for determining antigenicity profiles, and the Kyte-Doolittle technique, Kyte et al., *J. Mol. Biol.* (1982) 157:105–132 for hydropathy plots.

As used herein the term "T-cell epitope" refers to a feature of a peptide structure which is capable of inducing T-cell immunity towards the peptide structure or an associated hapten. T-cell epitopes generally comprise linear peptide determinants that assume extended conformations within the peptide-binding cleft of MHC molecules, (Unanue et al., *Science* (1987) 236:551–557). Conversion of polypeptides to MHC class II-associated linear peptide determinants (generally between 5–14 amino acids in length) is termed "antigen processing" which is carried out by antigen presenting cells (APCs). More particularly, a T-cell epitope is defined by local features of a short peptide structure, such as primary amino acid sequence properties involving charge and hydrophobicity, and certain types of secondary structure, such as helicity, that do not depend on the folding of the entire polypeptide. Further, it is believed that short peptides capable of recognition by helper T-cells are generally amphipathic structures comprising a hydrophobic side (for interaction with the MHC molecule) and a hydrophilic side (for interacting with the T-cell receptor), (Margalit et al., *Computer Prediction of T-cell Epitopes, New Generation Vaccines* Marcel-Dekker, Inc, ed. G. C. Woodrow et al., (1990) pp. 109–116) and further that the amphipathic structures have an $\alpha$-helical configuration (see, e.g., Spouge et al. *J. Immunol.* (1987) 138:204–212; Berkower et al. *J. Immunol.* (1986) 136:2498–2503).

Hence, segments of proteins which include T-cell epitopes can be readily predicted using numerous computer programs. (See e.g., Margalit et al., *Computer Prediction of T-cell Epitopes, New Generation Vaccines* Marcel-Dekker, Inc, ed. G. C. Woodrow et al., (1990) pp. 109–116). Such programs generally compare the amino acid sequence of a peptide to sequences known to induce a T-cell response, and search for patterns of amino acids which are believed to be required for a T-cell epitope.

An "immunological response" to a polypeptide or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition, such as an immunogenic composition, or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen or composition to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189–4199; Doe et al., *Eur. J. Immunol.* (1994) 24:2369–2376; and the examples below.

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic" polypeptide or composition is one which elicits an immunological response as defined above.

The term "antibody" as used herein includes antibodies obtained from both polyclonal and monoclonal preparations, as well as, the following: hybrid (chimeric) antibody molecules (see, for example, Winter et al. (1991) *Nature* 349:293–299; and U.S. Pat. No. 4,816,567); F(ab')$_2$ and F(ab) fragments; Fv molecules (non-covalent heterodimers, see, for example, Inbar et al. (1972) *Proc Natl Acad Sci USA* 69:2659–2662; and Ehrlich et al. (1980) *Biochem* 19:4091–4096); single-chain Fv molecules (sFv) (see, for example, Huston et al. (1988) *Proc Natl Acad Sci USA* 85:5879–5883); dimeric and trimeric antibody fragment constructs; minibodies (see, e.g., Pack et al. (1992) *Biochem* 31:1579–1584; Cumber et al. (1992) *J Immunology* 149B: 120–126); humanized antibody molecules (see, for example, Riechmann et al. (1988) *Nature* 332:323–327; Verhoeyan et al. (1988) *Science* 239:1534–1536; and U.K. Patent Publication No. GB 2,276,169, published 21 Sep. 1994); and, any functional fragments obtained from such molecules, wherein such fragments retain immunological binding properties of the parent antibody molecule.

A "recombinant" protein is a protein which retains the desired activity and which has been prepared by recombinant DNA techniques as described herein. In general, the gene of interest is cloned and then expressed in transformed organisms, as described further below. The host organism expresses the foreign gene to produce the protein under expression conditions.

A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, viral nucleic acid sequences, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

A "nucleic acid" sequence refers to a DNA or RNA sequence. The term captures sequences that include any of the known base analogues of DNA and RNA such as, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A "vector" is a replicon, such as a plasmid, phage, or cosmid, to which another nucleic acid segment may be attached so as to bring about the replication of the attached segment. A vector is capable of transferring gene sequences to target cells (e.g., bacterial plasmid vectors, particulate carriers, and liposomes).

Typically, the terms "vector construct," "expression vector," "gene expression vector," "gene delivery vector," "gene transfer vector," and "expression cassette" all refer to an assembly which is capable of directing the expression of a sequence or gene of interest. Thus, the terms include cloning and expression vehicles.

By "nonviral-mediated delivery" is meant the use of a vector construct, as defined above, which does not use an infectious viral vector system to gain entry into the host cell. Thus, gene delivery techniques using retrovirus, adenovirus, sindbus virus, adeno-associated virus, and the like, are considered viral-mediated delivery techniques herein. Generally, nonviral-mediated delivery refers to the use of a vector construct which includes the gene of interest operably linked to control elements which direct the expression of the gene of interest in vivo. The control elements can themselves be derived from viruses. One such nonviral-mediated delivery system involves the use of "naked" (plasmid) DNA. See, e.g., U.S. Pat. Nos. 6,214,804; 5,910,488; 5,589,466; 5,580,859, all of which are incorporated herein by reference in their entireties.

A "host cell" is a cell which has been transformed, or is capable of transformation, by an exogenous nucleic acid molecule.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

"Homology" refers to the percent similarity between two polynucleotide or two polypeptide moieties. Two DNA, or two polypeptide sequences are "substantially homologous" to each other when the sequences exhibit at least about 50%, preferably at least about 75%, more preferably at least about 80%–85%, preferably at least about 90%, and most preferably at least about 95%–98% sequence similarity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity and similarity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353–358, National biomedical Research Foundation, Washington, D.C., which adapts the local homology algorithm of Smith and Waterman *Advances in Appl. Math.* 2:482–489, 1981 for peptide analysis. Programs for determining nucleotide sequence similarity and identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity or similarity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

By "nucleic acid immunization" is meant the introduction of a nucleic acid molecule encoding one or more selected antigens into a host, for the in vivo expression of an antigen, antigens, an epitope, or epitopes. The nucleic acid molecule can be introduced directly into a recipient subject, such as by mucosal delivery such as oral and intranasal administration, or the like, or can be introduced ex vivo, into cells which have been removed from the host. In the latter case, the transformed cells are reintroduced into the subject where an immune response can be mounted against the antigen encoded by the nucleic acid molecule.

By "mucosal" delivery is meant delivery of an antigen to a mucosal surface, including oral, nasal, pulmonary, vaginal, rectal, urethral, and sublingual or buccal delivery.

The term "treatment" as used herein refers to either (1) the prevention of infection or reinfection (prophylaxis), or (2) the reduction or elimination of symptoms of the disease of interest (therapy).

By the terms "vertebrate," "subject," and "vertebrate subject" are meant any member of the subphylum Chordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds; and fish. The term does not denote a particular age. Thus, both adult and newborn animals, as well as fetuses, are intended to be covered.

B. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Central to the present invention is the discovery that oral fetal immunization with a DNA vaccine elicits humoral and cellular immune responses, thus reducing the high risk of neonatal infections. Experiments performed in support of the present invention have clearly demonstrated that a single DNA immunization induced both humoral and cellular immune responses in vaccinated animals. Moreover, immune memory was induced that responded to secondary immunization and viral infection. Furthermore, immune tolerance in non-responders was lacking. The observation that a single DNA injection induced active immunity has profound implications. In particular, the ability to avoid multiple immunizations clearly minimizes the risks associated with intrauterine injections. Moreover, the present results indicate that the fetal oral mucosa provides a very efficient site for DNA transfection.

The magnitude of the fetal immune responses in the present investigation was similar to that reported for 3 month old lambs following two intradermal injections of 500 µg of the same plasmid (Van Drunen Littel-van den Hurk, et al., *Viral Immunology* (1999) 12:67–77). This is surprising, since it is well known that intradermal application of plasmid DNA induces significantly better systemic immune responses than mucosal or oral application of plasmid DNA (McCluskie and Davis, *Crit. Rev. Immunol.* (1999) 19:303–329; Donelly, et al., *Annu Rev Immunol.* (1997) 15:617–648). Furthermore, delivery via the amniotic fluid provides a safe and relatively efficient method of DNA application that is effective without requiring formulation in exogenous transfection compounds.

The mucosal surfaces of the neonate are the primary site of entry for infectious agents during birth and the neonatal period. Thus, the induction of both systemic and mucosal immunity provides optimal protection against most infectious diseases of newborns. Recent observations suggest that both local and systemic immunity may contribute to immunity at mucosal surfaces (Baba, et al., *Nature Med.* (2000) 6:200–206; Mascola, et al., *Nature Med.* (2000) 6:207–210). In the examples detailed herein, mucosal immunity was evident in DNA-vaccinated fetuses through assays that detected gD-specific humoral (ASC) and cellular (LPR) immune responses in the lymph nodes draining the oral cavity. Moreover, gD-specific SIgA was present in nasal secretions of newborn lambs, confirming that in utero immunization induced mucosal immune responses. The presence of gD-specific serum antibody in all DNA-vaccinated fetuses was a clear indication of systemic immunity.

Additionally, the efficacy of oral DNA vaccination in utero was demonstrated herein using HBsAg plasmid DNA and protein vaccines. A single oral DNA vaccination induced higher protective antibody titres in more lambs and with less delay than did a single intramuscular injection of the recombinant protein vaccine. Protective levels of HBSAg-specific serum antibody developed when lambs were 3 weeks of age.

Taken together, these studies show the broad applicability of in utero DNA immunization. Immunization during the last trimester induces both mucosal and systemic immune responses. Moreover, in utero DNA immunization enhances both viral clearance and secondary immune response following respiratory tract infection and reduces the risk of vertical disease transmission through mucosal surfaces.

Mucosal immunity provides an important defense mechanism against a wide variety of pathogens. The mucosal surfaces of the gastrointestinal, respiratory and genitourinary tracts are continuously exposed to foreign antigens, including potentially infectious bacterial, viral and sometimes parasitic organisms. Mucosal immune responses protect against such challenges and have distinct and specialized characteristics.

For example, the principal immunoglobulin produced by the mucosal immune system is secretory IgA. Specialized antigen uptake cells in the Peyer's Patches of intestinal tract or nasopharyngeal lymphoid tissues, termed microfold or M cells, transport antigen to the underlying mucosal associated lymphoid tissues (MALT). In other areas of the mucosal epithelium, such as the pseudo-stratified airway epithelium, dendritic cells serve as antigen-presenting cells and migrate to local lymph nodes or MALT. Antigen processing and presentation occurs in the MALT, resulting in activation of antigen-specific IgA B cells. The subsequent trafficking and recirculation of the activated IgA B cells to other components of the mucosal immune system, e.g., the respiratory, intestinal and genital tracts, provides for disseminated local mucosal IgA responses throughout the "Common Mucosal System." Thus, the mucosal immune system is uniquely suited to respond to the types of antigenic challenge encountered by mucosal surfaces, and may provide the most effective type of immune response against particular pathogens. Accordingly, antigen delivery mechanisms which target the mucosal immune system provide an attractive means for achieving immunity.

A potential risk of immunizing fetuses and newborns is the induction of neonatal tolerance rather than the induction of an active immune response. However, since the first reports of neonatal immunization in 1997 (Sarzotti, et al., *Vaccine* (1997) 15:795–797; Prince, et al., *Vaccine* (1997) 15:916–919), several studies have demonstrated successful DNA immunization in newborn animals (Butts, et al., *Vaccine* (1998) 16:1444–1449). Although the underlying mechanisms of the induction of neonatal tolerance are still not completely understood, several parameters such as age, antigen dose and appropriate antigen presentation by dendritic cells might play an important role in developing neonatal nonresponsiveness (Ridge, et al., *Science* (1996) 271:1723–1726; Sarzotti, et al., *Science* (1996) 271:1726–1728; Forsthuber, et al., *Science* (1996) 271:1728–1730). So far, only immunization with the gene encoding the *Plasmodium yoelii* malaria circumsporozoite protein (CSP) has induced neonatal tolerance in newborn mice (Mor, et al., *J. Clin. Invest.* (1996) 98:2700–2705; Ichino, et al., *J. Immunol.* (1999) 162:3814–3818; Isshii, et al., *Vaccine* (2000) 18:703–710). Induction of neonatal tolerance, as determined by the lack of a humoral or cellular response to a second DNA-injection after 6 weeks, was observed only after DNA immunization and not after immunization with a recombinant protein (Mor, et al., supra). The development of tolerance also seemed to be age- (<7days) and dose-dependent (10–100 μg plasmid per mouse), but was not MHC-restricted (Ichino, et al., supra). Interestingly, CD8+ T cells from tolerant mice tranferred the induced nonresponsiveness to naive recipients, which might indicate the involvement of suppressor T cells (Ichino, et al., supra). The same investigators showed, however, that co-administration of a plasmid encoding the granulocyte-macrophage colony stimulating factor (GM-CSF) prevented the development of neonatal tolerance and elicited a primary IgG anti CSP immune response (Isshii, et al., supra).

In contrast to this, the results provided herein clearly demonstrate that fetuses responded to the injection of plasmid-DNA and inactivated antigen with gD-specific IgG1-antibodies. The antibody titers induced in fetuses were higher than those observed following intradermal immunization of neonates with the same dose of the same plasmid. DNA immunized neonates also responded to a secondary DNA immunization at a later date (Van Drunen Littel-van den Hurk, et al., *Viral Immunology* (1999) 12:67–77). These observations support the conclusion that DNA immunization of the late term fetus with an antigen-encoding gene, such as the herpesvirus gD gene or the hepatitis B surface antigen, should not induce neonatal tolerance.

DNA vaccination provides several inherent advantages (Donely, et al., *Annu Rev Immunol.* (1997) 15:617–648). The endogenous synthesis of an encoded antigen facilitates both MHC-I and MHC-II restricted antigen presentation, which is necessary for the in vivo generation of both cell-mediated and humoral immune responses. For example, in the examples detailed herein, DNA-vaccination was clearly more efficient than immunization with the corresponding purified antigen. All DNA-vaccinated fetuses displayed higher serum antibody titers and antigen-specific proliferative responses in blood and retropharyngeal lymph nodes, and there was no detectable mucosal immunity following immunization with inactivated virus (Table 1, FIGS. 1A and 1B). The endogenous synthesis of encoded proteins also ensures appropriate processing and conformation of viral proteins, which is particularly important for the generation of neutralizing antibodies (Van Drunen Littel-van den Hurk, et al., *Vaccine* (1992) 11:25–35). Previous studies have demonstrated that for alphaherpesviruses the conformation of the glycoprotein gD is a criticial parameter for the induction of protective immunity (Van Drunen Littel-van den Hurk, et al., *Vaccine* (1992) 11:25–35). The appropiate expression of glycoprotein D in immunized fetuses was confirmed herein by the induction of neutralizing serum antibodies (Table 1). Thus, DNA vaccination of the fetus induced a humoral immune response that should protect against viral infection.

Unlike viral vectors, DNA vaccines can be injected repeatedly to effectively boost the level of an immune response (Donelly, et al., *Annu Rev Immunol.* (1997) 15:617–648). This is of particular importance, since Iwamoto et al., *Gene Ther.* (1999) 6:98–106, recently showed that the repeated in utero delivery of an E1,E3-deleted adenoviral vector, encoding β-galactosidase, resulted in over 50% mortality in fetal lambs. Therefore, a second vaccination at birth, even with other types of vaccines, such as a subunit or modified live vaccines, could enhance the level of disease protection, acquired by neonates, who face a high risk of disease transmission. Moreover, a primary fetal immunization combined with secondary immunization at birth may confer protective immunity against the typical "first week-infections", such as human respiratory syncyti-cal virus (Henderson, F. W. in *Rudolph's Pediatrics* 1996 (Rudolph, A. M., et al., eds.) pp. 536–544, Appleton & Lange, Stamford, Conn.).

Fetal sheep, the animal model used herein, provide an excellent model for studying several aspects of the ontogeny of immunity (Hein, W. R., *The Immunologist* (1995) 3:12–18) as well as new approaches for gene therapy (Zanjani, et al., *Science* (1999) 285:2084–2088) and human stem cells transplantation (Sekhon and Larson, *Nature. Med.* (1995) 11:1201–1203). In contrast to mice and rats, where the immune system undergoes very little peripheral expansion prior to birth, the peripheral lymphoid organs of sheep and humans undergo substantial development during fetal life (Griebel and Hein *Immunology Today* (1996) 17:30–39). Furthermore, sheep and humans show significant similarities in the appearance of leukocytes in circulation during fetal development (Alsalami, et al., *Aust. Vet. J.* (1999) 77:588–594). Immune responsiveness develops in fetal lambs by mid-gestation, and depending on the type of antigen, the capacity to perform isotype-switching has developed prior to the last trimester of gestation (Griebel, P. J. in *Handbook of Vertebrate Immunology* 1998 (Pastoret, et al., eds) pp. 485–554 (Academic Press, San Diego/London). In addition, the size of the fetal lamb during the last trimester of gestation facilitates a variety of experimental interventions. Thus, fetal sheep provide an appropiate model for investigating in utero immunization and making predictions from the results obtained using this animal model.

In order to further an understanding of the invention, a more detailed discussion is provided below regarding particular antigens for use with the subject methods, as well as methods of obtaining and delivering the compositions.

In particular, as explained above, the method of the invention results in both cell-mediated immunity as well as humoral antibody responses. Thus, in addition to a conventional antibody response, the system herein described provides for, e.g., the association of the expressed antigens with class I MHC molecules such that an in vivo cellular immune response to the antigen of interest can be mounted which stimulates the production of CTLs to allow for future recognition of the antigen. Furthermore, the method is capable of eliciting an antigen-specific response by helper T-cells. Accordingly, the methods of the present invention will find use with any antigen for which both cellular and humoral immune responses are desired, including antigens derived from viral, bacterial, fungal and parasitic pathogens that may induce antibodies, T-cell helper epitopes and T-cell cytotoxic epitopes. Such antigens include, but are not limited to, those encoded by human and animal viruses and can correspond to either structural or non-structural proteins.

The technique is particularly useful for immunization against intracellular viruses which normally elicit poor immune responses. Additionally, immunization against pathogens that threaten newborns is particularly desirable. Thus, the methods described herein will find use for immunizing against a wide variety of organisms, such as viral, bacterial, mycoplasm, parasitic and even tumor antigens, as well as allergens.

For example, the present invention will find use for stimulating an immune response against a wide variety of proteins from the herpesvirus family, including proteins derived from bovine herpes virus (BHV) and human herpes simplex virus (HSV) types 1 and 2, such as BHV-1, BHV-2, HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human and animal herpesviruses such as HHV6 and HHV7. (See, e.g. Chee et al., *Cytomegaloviruses* (J. K. McDougall, ed., Springer-Verlag 1990) pp. 125–169, for a review of the protein coding content of cytomegalovirus; McGeoch et al., *J. Gen. Virol.* (1988) 69:1531–1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207–211, for the identification of protein coding sequences in an EBV genome; and Davison and Scott, *J. Gen. Virol.* (1986) 67:1759–1816, for a review of VZV.) Additionally, immunization against various hepatitis viruses, such as HBV, using, for example, hepatitis B surface antigen (HBsAg), as well as any of the various human papilloma viruses, rotaviruses, etc., will find use with the present methods.

Polynucleotide sequences encoding antigens derived from other viruses will also find use in the claimed methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabdoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIB}$, $HIV_{SF2}$, $HIV_{LAV}$, $HIV_{LAI}$, $HIV_{MN}$); $HIV-1_{CM235}$, $HIV-1_{US4}$; HIV-2; simian immundeficiency virus (SIV) among others. See, e.g. Virology, 3rd Edition (W. K. Joklik ed. 1988); *Fundamental Virology*, 2nd Edition (B. N. Fields and D. M. Knipe, eds. 1991), for a description of these and other viruses.

Antigens derived from fungal pathogens, bacterial pathogens, such as from *Mycobacterium leprae, M. tuberculosis, Borrelia burgdorferi, Bordetella pertussis, Clostridium tetani, Streptococcus, Salmonella typhimurium, S. enterica, Shigella, E. coli, Hemophilus influenzae*, and the like will also find use herein. Similarly, antigens from *Mycoplasm*, such as *M. pulmonis*; parasitic antigens, such as from *Plasmodium yoelii, P. falciparum, Toxoplasma gondii, Schistosoma japonicum, Leishmania major, Trypanosoma cruzi*, and so forth, can be used with the subject methods.

The techniques can be used for the delivery of discrete antigens, larger portions of the genome in question and, for example, a proviral DNA which includes nearly all of the viral genome. It is readily apparent that the subject invention can be used to prevent or treat a wide variety of diseases.

Additionally, rather than delivering the nucleic acid sequences encoding the antigens, nucleic acid sequences encoding recombinant antibodies may also be delivered by the subject methods.

Polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from cells and tissues containing the same, using standard techniques, such as phenol extraction and PCR of cDNA or genomic DNA. See, e.g., Sambrook et al., supra, for a description of techniques used to obtain and isolate DNA. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence is assembled from overlapping oligonucleotides prepared by standard methods and assembled into a complete coding sequence. See, e.g., Edge, *Nature* (1981) 292:756; Nambair et al., *Science* (1984) 223:1299; Jay et al., *J. Biol. Chem.* (1984) 259:6311.

Next, the gene sequence encoding the desired antigen can be inserted into a vector which includes control sequences operably linked to the desired coding sequence, which allow for the expression of the gene in vivo in the subject species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence. Introns, containing splice donor and acceptor sites, may also be designed into the constructs for use with the present invention.

Enhancer elements may also be used herein to increase expression levels of the mammalian constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence.

Furthermore, plasmids can be constructed which include a chimeric gene sequence, encoding e.g., multiple antigens of interest, for example derived from more than one viral isolate. Additionally, genes coding for immune modulating agents which can enhance antigen presentation, attract lymphocytes to the site of gene expression or promote expansion of the population of lymphocytes to the site of gene expression or promote expansion of the population of lymphocytes which respond to the expressed antigen, can also be present. Such agents include cytokines, lymphokines, and chemokines, including but not limited to IL-2, modified IL-2 (cys125→ser125), GM-CSF, IL-12, γ-interferon, IP-10, MIP1α, MIP1β and RANTES. Additionally, immune molecules such as TAP transporters, costimulatory molecules such as B7, β2M, class I or II MHC genes (syngeneic or allogeneic), and other genes coding for proteins that are required for efficient immune responses but are not expressed due to specific inhibition or deletion, will also find use in the constructs.

The above sequences can be administered using separate vectors or can be present on the vector bearing the gene encoding the antigen of interest. If present on the same vector, the additional gene sequences can either precede or follow the gene encoding the antigen of interest in a dicistronic gene configuration. Additional control elements can be situated between the various genes for efficient translation of RNA from the distal coding region. Alternatively, a chimeric transcription unit having a single open reading frame encoding both the gene of interest and the modulator, can also be constructed. Either a fusion can be made to allow for the synthesis of a chimeric protein or alternatively, protein processing signals can be engineered to provide cleavage by a protease such as a signal peptidase, thus allowing liberation of the two or more proteins derived from translation of the template RNA. Such signals for processing of a polyprotein exist in, e.g., flaviviruses, pestiviruses such as HCV, and picornaviruses, and can be engineered into the constructs. The processing protease may also be expressed in this system either independently or as part of a chimera with the antigen and/or cytokine coding region(s). The protease itself can be both a processing enzyme and a vaccine antigen.

Once complete, the constructs are used for nucleic acid immunization using standard gene delivery protocols. Methods for gene delivery are known in the art. See, e.g., U.S. Pat. Nos. 5,399,346, 5,580,859, 5,589,466. Genes can be delivered either directly via the amniotic fluid to the vertebrate subject or, alternatively, delivered ex vivo, to cells derived from the subject and the transformed cells delivered to the subject. Ultrasound guided vaccine delivery (Greenwood, et al., *Reprod. Fert. Develop.* (1999) 11:303) can be used to aid with in utero delivery. Moreover, the genes can be delivered with or without a viral vector.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, *BioTechniques* (1989) 7:980–990; Miller, A. D., *Human Gene Therapy* (1990) 1:5–14; Scarpa et al., *Virology* (1991) 180:849–852; Burns et al., *Proc. Natl. Acad. Sci. USA* (1993) 90:8033–8037; and Boris-Lawrie and Temin, *Cur. Opin. Genet. Develop.* (1993) 3:102–109.

A number of adenovirus vectors have also been described. Unlike retroviruses which integrate into the host genome, adenoviruses persist extrachromosomally thus minimizing the risks associated with insertional mutagenesis (Haj-Ahmad and Graham, *J. Virol.* (1986) 57:267–274; Bett et al., *J. Virol.* (1993) 67:5911–5921; Mittereder et al., *Human Gene Therapy* (1994) 5:717–729; Seth et al., *J. Virol.* (1994) 68:933–940; Barr et al., *Gene Therapy* (1994) 1:51–58; Berkner, K. L. *BioTechniques* (1988) 6:616–629; and Rich et al., *Human Gene Therapy* (1993) 4:461–476).

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 published 23 Jan. 1992) and WO 93/03769 (published 4 Mar. 1993); Lebkowski et al., *Molec. Cell. Biol.* (1988) 8:3988–3996; Vincent et al., *Vaccines* 90 (1990) (Cold Spring Harbor Laboratory Press); Carter, B. J. *Current Opinion in Biotechnology* (1992) 3:533–539; Muzyczka, N. *Current Topics in Microbiol and Immunol.* (1992) 158:97–129; Kotin, R. M. *Human Gene Therapy* (1994) 5:793–801; Shelling and Smith, *Gene Therapy* (1994) 1:165–169; and Zhou et al., *J. Exp. Med.* (1994) 179:1867–1875.

A vaccinia based infection/transfection system can be conveniently used to provide for inducible, transient expression of the gene of interest in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, *Proc. Natl. Acad. Sci. USA* (1990) 87:6743–6747; Fuerst et al., *Proc. Natl. Acad. Sci. USA* (1986) 83:8122–8126.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, *J. Mol. Biol.* (1986) 189:113–130; Deng and Wolff, *Gene* (1994) 143:245–249; Gao et al., *Biochem. Biophys. Res. Commun.* (1994) 200:1201–1206; Gao and Huang, *Nuc. Acids Res.* (1993) 21:2867–2872; Chen et al., *Nuc. Acids Res.* (1994) 22:2114–2120; and U.S. Pat. No. 5,135,855.

The gene of interest can also be delivered without a viral vector. For example, the gene can be delivered directly to the subject or packaged in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097:1–17; Straubinger et al., in *Methods of Enzymology* (1983), Vol. 101, pp. 512–527.

Liposomal preparations for use in the instant invention include cationic (positively charged), anionic (negatively charged) and neutral preparations, with cationic liposomes particularly preferred. Cationic liposomes have been shown to mediate intracellular delivery of plasmid DNA (Felgner et al., *Proc. Natl. Acad. Sci. USA* (1987) 84:7413–7416); mRNA (Malone et al., *Proc. Natl. Acad. Sci. USA* (1989) 86:6077–6081); and purified transcription factors (Debs et al., *J. Biol. Chem.* (1990) 265:10189–10192), in functional form.

Cationic liposomes are readily available. For example, N-[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., *Proc. Natl. Acad. Sci. USA* (1987)

84:7413–7416). Other commercially available lipids include transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194–4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512–527; Szoka et al., *Proc. Natl. Acad. Sci. USA* (1978) 75:4194–4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem.* (1980) 255:10431; Szoka and Papahadjopoulos, *Proc. Natl. Acad. Sci. USA* (1978) 75:145; and Schaefer-Ridder et al., *Science* (1982) 215:166.

The DNA can also be delivered in cochleate lipid compositions similar to those described by Papahadjopoulos et al., *Biochem. Biophys. Acta*. (1975) 394:483–491. See, also, U.S. Pat. Nos. 4,663,161 and 4,871,488.

The gene of interest may also be delivered using particulate systems and polymers. For example, polymers such as polylysine, polyarginine, polyomithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Felgner, P. L., *Advanced Drug Delivery Reviews* (1990) 5:163–187, for a review of delivery systems useful for gene transfer.

Additionally, biolistic delivery systems employing particulate carriers such as gold and tungsten, are especially useful for delivering genes of interest. The particles are coated with the gene to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744.

The recombinant vectors (with or without associated lipids or carriers) are formulated into compositions for delivery to the vertebrate subject. Methods of preparing such formulations are described in, e.g., *Remington's Pharmaceutical Sciences*, Mack Publishing Company, Easton, Pa., 18 Edition, 1990. These compositions may either be prophylactic (to prevent infection) or therapeutic (to treat disease after infection). The compositions will comprise a "therapeutically effective amount" of the gene of interest such that an amount of the antigen can be produced in vivo so that an immune response is generated in the individual to which it is administered. The exact amount necessary will vary depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials. For example, for purposes of the present invention, an effective dose will be from about 1 $\mu$g to about 100 mg, more preferably from about 10 $\mu$g to about 1 mg, of the DNA constructs.

The compositions will generally include one or more "pharmaceutically acceptable excipients or vehicles" appropriate for mucosal delivery, such as water, saline, glycerol, polyethyleneglycol, hyaluronic acid, ethanol, etc. Additionally, auxiliary substances, such as wetting or emulsifying agents, pH buffering substances, and the like, may be present in such vehicles. Certain facilitators of nucleic acid uptake and/or expression can also be included in the compositions or coadministered, such as, but not limited to, bupivacaine, cardiotoxin and sucrose.

For example, intranasal and pulmonary formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

For rectal and urethral suppositories, the vehicle composition will include traditional binders and carriers, such as, cocoa butter (theobroma oil) or other triglycerides, vegetable oils modified by esterification, hydrogenation and/or fractionation, glycerinated gelatin, polyalkaline glycols, mixtures of polyethylene glycols of various molecular weights and fatty acid esters of polyethylene glycol.

For vaginal delivery, the formulations of the present invention can be incorporated in pessary bases, such as those including mixtures of polyethylene triglycerides, or suspended in oils such as corn oil or sesame oil, optionally containing colloidal silica. See, e.g., Richardson et al., *Int. J. Pharm.* (1995) 115:9–15.

For a further discussion of appropriate vehicles to use for particular modes of delivery, see, e.g., *Remington: The Science and Practice of Pharmacy*, Mack Publishing Company, Easton, Pa., 19th edition, 1995. One of skill in the art can readily determine the proper vehicle to use for the particular antigen and site of delivery.

Once formulated, the compositions of the invention can be administered directly to the subject or, alternatively, delivered ex vivo, to cells derived from the subject, using methods such as those described above. For example, methods for the ex vivo delivery and reimplantation of transformed cells into a subject are known in the art and will include e.g., dextran-mediated transfection, calcium phosphate precipitation, polybrene mediated transfection, lipofectamine and LT-1 mediated transfection, protoplast fusion, electroporation, encapsulation of the polynucleotide(s) in liposomes, and direct microinjection of the DNA into nuclei.

Direct delivery of the compositions in vivo will generally be accomplished with or without viral vectors, as described above, by injection using a conventional syringe or a gene gun, such as the Accell® gene delivery system (Agracetus, Inc., Middleton, Wis.). The constructs are injected mucosally, such as orally, via the amniotic fluid. The constructs may be delivered into cells of the epidermis which provides access to skin-associated lymphoid cells and provides for a transient presence of DNA in the vaccine recipient.

Dosage treatment may be a single dose schedule or a multiple dose schedule. For example, the first vaccine is normally given after the fetal immune system has developed to a point that renders it capable of developing an immune response and development has progressed to a stage that makes administration feasible. The organs which function in the immune system need not be completely developed at the time of the first vaccination. The time for delivery will depend on the particular species of subject in question. Thus, the DNA vaccines described herein will normally be delivered at least half-way through the gestational period, more preferably in the last trimester, but can be delivered earlier.

As shown herein, immune responses are boostable with one or more injections given at birth or shortly thereafter, such as at birth or 1 day to 14 days or more after birth. Subsequent boosts can also be administered. The subsequent vaccine can be the same or different than the vaccine delivered in utero. Thus, the identical nucleic acid vaccine can be delivered. Alternatively, a subunit vaccine containing the antigen encoded by the nucleic acid can be delivered, or even an attenuated bacterium or virus can be used for the boost.

C. Experimental

Below are examples of specific embodiments for carrying out the present invention. The examples are offered for illustrative purposes only, and are not intended to limit the scope of the present invention in any way. Those of skill in the art will readily appreciate that the invention may be practiced in a variety of ways given the teaching of this disclosure.

Efforts have been made to ensure accuracy with respect to numbers used (e.g., amounts, temperatures, etc.), but some experimental error and deviation should, of course, be allowed for.

Materials and Methods

In the following methods, restriction and modifying enzymes, as well as other reagents for DNA manipulations were purchased from commercial sources, and used according to the manufacturers' directions. In the cloning of DNA fragments, except where noted, all DNA manipulations were done according to standard procedures. See, e.g., Sambrook et al., supra.

Cells and viruses: Bovine viral diarrhea virus-free Madin Darby bovine kidney (MDBK) cells were cultured in minimum essential medium (MEM; GibcoBRL, Burlington, ON, Canada) supplemented with 5% fetal bovine serum (FBS; GibcoBRL). BHV-1 strain 108, is a virulent field isolate (Jericho, et al., *Can. J. Comp. Med.* (1978) 42:156–167) and was propagated in MDBK cells.

Plasmids: Generation of the pSLIAtgD plasmid was described previously by Braun et al. (*Vaccine Res.* (1997) 6:151–164). The gene encoding the truncated version of BHV-1 gD was inserted into plasmid pSLIA0 under the control of the human cytomegalovirus (HCMV) immediate early promotor/1A-region. Plasmids were transformed into *E. coli* DH5α and purified using the Qiagen Giga-Kit (Qiagen, Mississauga, ON). DNA concentration was estimated after agarose gel electrophoresis by comparison with known standards and by spectrophotometry. Plasmid pMCG-16-16HBsAg was a generous gift from Drs. Heather L. Davis and Risini Weeratna (Loeb Research Institute, Ottawa, ON Canada) and contained the open reading frame of the HBV-S gene flanked by the CMV promoter and downstream with a bovine growth hormone polyA region; in addition the plasmid contained 16 copies of a murine CpG immunostimulatory motif. For immunization, DNA was dissolved in pyrogen-free PBS, pH 7.3 (Sigma-Aldrich, Oakville, ON, Canada).

Inactivation of BHV-1 by UV-irradiation: BHV-1 was inactivated by UV-irradiation as described previously (Popowych, Y. I. An assessment of in vitro assays used to detect BHV-1 specific CMI responses. (1994) Thesis, Department of Veterinary Microbiology, University of Saskatchewan, Saskatoon). Briefly, one ml of $1\times10^8$ p.f.u. of BHV-1 was inactivated in a cabinet fitted with a germicidal fluorescent bulb (G8T5, General Electronic) with a UV-dose of 3260 mJ/$cm^2$. Complete inactivation was verified in a virus-plaque assay.

Fetal immunization: Suffolk sheep were obtained from the Department of Animal and Poultry Science, University of Saskatchewan. The ewes were bred following estrus synchronization with medoxyprogesterone acetate (Veramix, Upjohn, Orangeville, ON) and injection with pregnant mare serum gonadotrophin (Equinex, Ayerst, Winnipeg, MB). Pregnancy was confirmed by ultrasound at day 45 and 105 of gestation and fetal immunization was then performed at days 121–124 of gestation. Briefly, ewes were anaesthetized as described previously (Mutwiri, et al., *Immunology* (1999) 97:455–461) and positioned in dorsal recumbancy with a slight rotation to the right side. A ventral midline incision was made in the abdomen and both uterine horns were palpated to verify the presence of a single or two fetuses. Subsequently, the head of the fetus was positioned with the uterine wall compressed against the commissure of the fetal mouth. The fetal mouth was opened and 5 ml of DNA-solution or sterile PBS were injected using a 23 g-needle inserted through the uterine wall and positioned in the fetal oral cavity. This injection was followed with 500 mg of ampicillin (250 mg/ml; Novopharm, Toronto, ON).

The recombinant HBsAg protein vaccine (Engerix-B™; SmithKline Beecham Pharma Inc., Oakville, ON, Canada) was injected intramuscularly by palpating the hindleg of the fetus and inserting a 23 g needle through the uterine wall and into the ischiatic muscles.

For injection of the inactivated BHV-1, the fetus was positioned with its right side underlying the uterine wall. A 2 cm incision was made through the uterine wall, without disrupting the amniotic membrane. A purse-string suture with 4-0 PDS (Ethicon, Peterborough, ON) was placed in the amniotic membrane at the margins of the uterine incision. The amniotic membrane was incised in the centre of the purse-string suture and forceps were used to raise a fold of skin on the neck of the fetus. One ml each of irradiated BHV-1 ($2.5\times10^7$ p.f.u.) was injected subcutaneously at the base of the skinfold and into the oral cavity followed by a second oral injection of 500 mg ampicillin. The purse-string suture was used to close the amnitoic membranes and the uterine wall was closed with #1 Vicryl (Serag-Wiesner, Naile, Germany). Following fetal immunization, the uterus was returned to the abdominal cavity and the incision was closed as previously described (Mutwiri, et al., *Immunology* (1999) 97:455–461). At day 142 or 143 of gestation all ewes were anaestetized with Pentobarbital. The fetuses were exposed, and euthanized prior to tissue collection.

Immunization of lambs: Newborn lambs (1–4 days old) were immunized intradermally with 500 μg of pSLIA-tgD plasmid, resuspended in 500 μl of PBS, or with 500 μl of PBS alone. The vaccine injection site was on the lateral aspect of the lower mandible since lymph draining from this area collects in the retropharyngeal lymph nodes (Sisson and Grossman (eds.) 1953. *The Anatomy of Domestic Animals*. 4th edition, W. B. Saunders, Philadelphia. pp. 735). Lambs without a detectable response to in utero DNA immunization were evaluated for gD-specific immune tolerance by immunizing the lamb with an inactivated, commercial BHV-1 vaccine (Triangle 3; Ayerst Vet. Lab., Guelph, ON, Canada). The vaccine was injected intramuscularly following the manufacturer's guidelines and each lamb received the equivalent of three bovine doses.

Collection of nasal secretions: Nasal secretions were collected with three absorptive swabs (Merocel; Solan Xomed, Jacksonville, Fla.) after spraying 150 μl PBS into each nostril. The swabs were placed proximal to the external nares to absorb fluid without disrupting the nasal mucosa. Nasal swabs were placed in 1.5 ml Eppendorf tubes (Brinkmann Instruments Inc., Mississauga, ON, Canada) and kept on ice. Tubes were pierced at the bottom, placed inside a second tube containing 10μ of 0.1M PMSF (Sigma-Aldrich) and centrifuged for 30 s at 15850×g.

Challenge infection: Each lamb was challenged with 5–7×10$^7$ PFU of BHV-1 strain 108 by covering the nostrils and the oral cavity with an inhalation mask and aerosolizing the virus for 4 min with a DeVILBISS™ Nebulizer (Model 099HC; The DeVILBISS Co., Somerset, Pa.).

Virus isolation: Nasal secretions were collected daily for 8 days p.i. by placing a sterile cotton swab in the left nostril. The cotton swab was saturated with nasal secretions and then placed into one ml MEM medium (Gibco BRL) and stored at −70° C. Infectious virus recovered from each swab was quantified by plaque titration as described previously (Rouse and Babiuk, *J. Immunol.* (1974) 113:139).

Serum cortisol assay: Serum cortisol analysis was performed in the Endocrine Laboratory, Prairie Diagnostic Services, Western College of Veterinary Medicine (WCVM), Saskatoon, Saskatchewan. Serum samples were stored at −70° C. until analyzed using a fluorescence polarization immunoassay (TDx System, Abbott Laboratories, Irving, Tex.).

ELISA: Polystyrene microtiter plates (Immunolon II, Dynatech Laboratories, Gaithersburg, Md.) were coated with 0.1 μg of affinity purified tgD or tgB per well and incubated with serially diluted fetal, lamb or ewe sera. The mouse anti-bovine IgG1 monoclonal antibody BIG715A (VMRD Inc, Pullman, Wash.; 1:4000 dilution), alkaline-phosphatase (AP)-conjugated or biotin-conjugated rabbit anti-sheep IgG (Kirkegaard and Perry Laboratories, Gaithersburg, Md.; 1:6000 dilution), or AP-conjugated rabbit anti-sheep IgM (Kirkegaard and Perry Laboratories, Gaithersburg, Md.; 1:10000 dilution) were used to detect total gD or gB captured sheep Ig. Rabbit anti-sheep IgA specific antibody (Bethyl; 1:2000 dilution) was purified, biotinylated and used to detect gD-specific IgA in nasal secretions. The reaction was amplified using the AP-streptavidin complex (GibcoBRL, Burlington, ON; 1:2000 dilution) and visualized with p-nitrophenyl phosphate (PNPP, Sigma-Aldrich, Oakville, ON).

Western blotting: The presence of gD- and gB-specific antibodies in the sera of immunized lambs was also assessed by Western blotting. Briefly, purified gD or gB was transferred to nitrocellulose after electrophoretic separation on a 8.5% polyacrylamide gel. After blocking, filters were incubated overnight in serum (1:50 dilution in Tris buffered saline, TBS) and bound antibody was visualized with alkaline phosphatase conjugated goat anti-mouse (Kirkegaard Perry Laboratories, 1:5000) or rabbit anti-sheep antisera (Kirkegaard Perry Laboratories; diluted 1:5000) using BCIP/NBT (Sigma-Aldrich). Monoclonal antibodies specific for BHV-1 gB and gD were used (Van Drunen Littel-van den Hurk, et al., *J. Gen. Virol.* (1998) 79:831). HBsAg-specific antibody titres were assayed using a Microparticle Enzyme Immunoassay (Abbot IMX AUSAB; ABBOT Laboratories Ltd., Diagnostic Division, Mississauga, ON, Canada) and the assay was read using the Abbot IMX kit and analyzer (ABBOT Laboratories Ltd.).

Virus Neutralization test: After addition of 5% rabbit serum as a source of complement, twofold serial dilutions of the non heat-inactivated test sera in medium were mixed with ca. 50 TCID$_{50}$ BHV-1 strain 108 in a final volume of 100 μl and incubated for 17 hours at 37° C. Thereafter, 100 μl of MDBK cells, corresponding to 1–2×10$^4$ cells per well, were added to each sample and cells were incubated for 4 days at 37° C. and 5% CO$_2$. Cells were assessed for BHV-1 specific cytopathic effect and serum neutralization titer was indicated as the highest serum dilution to achieve complete virus neutralization.

Flow cytometry and clinical pathology: Monoclonal antibodies (mAb) specific for sheep IgM (Clone PIg45A), IgG1 (Clone BIg715A), CD25 (Clone CACT116) and MHC II (Clone TH14B) were purchased from VMRD Inc. (Pullman, WA). The CD5 (Clone ST1a), CD4 (Clone 17D-13), CD8 (Clone E95), and γδ TcR (Clone 86D) specific mAbs were produced from hybridomas from Dr. Wayne Hein (AgResearch, Wallaceville, NZ). Fluorescein isothiocyanate (FITC)-conjugated and phycoerythrin (PE)-conjugated, isotype-specific goat anti-mouse Ig antibodies were purchased from Southern Biotechnology (Birmingham, Ala.). Flow cytometric analyses were restricted to viable cells by excluding cells stained with propidium iodide (2.5 μg/ml; FL3). Specific mAb staining was determined by subtracting cells reacting with isotype-matched and concentration-matched (1–10 μg/ml) irrelevant mAbs (Caltag Lab., Burlingame, Calif.). All samples were analyzed with a FACScan (Becton Dickinson, Mountain View, Calif.) flow cytometer and the Cell Quest program was used for data acquisition and analysis. The analysis of total white blood cell counts and differential counts of lymphocyte, monocyte and polymorphonuclear cell populations were performed by Prairie Diagnostic Services (Western College of Veterinary Medicine, Saskatoon, SK Canada).

Lymphoproliferative response (LPR): Blood was collected in EDTA-treated vacutainers (Becton Dickonson, Franklin Lakes, N.J.) and mononuclear cells were isolated as described previously (Dudler, et al., in *Immunological methods manual*. 1997 (Lefkovits, I., ed.) Vol. 4, pp. 2075–2078 (Academic press, San Diego/London). Lymphocytes were isolated from the lymph nodes and used for LPR and antibody secreting cells assay as previously described (Mutwiri, et al., *Immunology* (1999) 97:455–461). Briefly, cell suspensions were cultured in serum-free medium (AIM-V, GibcoBRL) supplemented with 2% fetal bovine serum (GibcoBRL) and 20 μM 2-mercaptoethanol (Sigma-Aldrich). LPR were conducted with 3×10$^5$ cells/well (microtiter plates, NUNC, Nalgen Nunc International Corporation, Naperville, Ill.) in a final volume of 200 μl medium. Triplicate cultures were stimulated with 100 μl purified gD (0.2 μg/ml, 2 μg/ml, 2.5 μg/ml or 5 μg/ml), 1

μg/ml ConA (Sigma-Aldrich; 1 μg/ml) or medium alone. After 3 days incubation, the cells were incubated with [methyl-$^3$H]thymidine (Amersham Pharmacia Biotech Inc, Baie de Urfe, QC) at a concentration of 0.4 μCi/well for 16 hours. Cells were harvested following standard liquid scintillation protocols. Proliferative responses were calculated as the mean of triplicate cultures and expressed as a stimulation index (SI=counts per min in the presence of antigen/counts per min in the absence of antigen).

Antibody secreting cell assay: The gD-specific antibody-secreting cells were detected using a modified ELISPOT assay, as previously described (Mutwiri, et al., *Immunology* (1999) 97:455–461). Briefly, microtiter nitrocellulose filtration plates were coated overnight with 1 μg/ml purified tgD. Unbound protein was removed and 1×10$^6$ cells from individual lymph nodes were added to triplicate wells, in a final volume of 200 μl culture medium. After 18 hours incubation at 37° C. in a humidified atmosphere with 5% $CO_2$ the cells were removed and plates were incubated with biotinylated rabbit anti-sheep IgG (H and L chain-specific, Kirkegaard and Perry Larboratories, Gaithersburg, Md.; 1:6000 dilution). Subsequently, the plates were incubated with AP-conjugated streptavidin (Jackson Immunoresearch, Lab. Inc, Westgrove, Pa.; 1:1000 dilution) and then developed with 5-bromo-4-chloro-3-indolyl phosphate/nitroblue tetrazolium (BCIP/NBT) insoluble alkaline phosphatase substrate (Sigma-Aldrich). The frequency of gD-specific ASC per 1×10$^6$ cells was calculated by subtracting the number of ASC detected in wells not coated with antigen from the number of ASC detected in tgD-coated wells. An inverted light microscope was used to count three replicates for each tissue and data presented are mean values for individual lymph nodes.

Statistical Analysis: Data for serum antibody titres and virus shedding in nasal secretions were transformed to $\log_{10}$ before performing a one-way analysis of variance (ANOVA) for data at each time point. Data for LPR were also analysed with one-way ANOVA to compare responses within assays conducted at each time point. When ANOVA indicated a significant difference among means, Tukey's multiple comparison test was used to identify groups that were significantly different. All statistical analyses were performed using GRAPHPAD PRISM 2.01 SOFTWARE (Graphpad Software, Inc., San Diego, Calif.).

EXAMPLE 1

Safety of Fetal Nucleic Acid Immunization

In order to test the safety of oral fetal DNA immunization, vaccine delivery into the amniotic fluid in the oral cavity was performed with nine pregnant ewes at day 123 or 124 of pregnancy (148 day gestation). Four fetuses were immunized with a single injection of 500 μg tgD-encoding plasmid and four fetuses received PBS. One fetus was immunized with 5×10$^7$ plaque forming units (p.f.u.) of inactivated bovine herpesvirus-1 (BHV-1). Half of the BHV-1 was injected subcutaneously and half was injected into the amniotic fluid in the oral cavity. Following surgery, none of the ewes displayed clinical signs of illness and there were no fetal deaths or abortions. Fetal lambs were of normal size and displayed normal organ development when tissues were collected at day 145 or 146 of gestation. Histological examination did not reveal pathological changes in any of the fetuses.

To further investigate the effect of DNA vaccination on the fetal development, the level of cortisol in fetal serum was measured. During normal gestation, the level of fetal serum cortisol begins to increase after day 125 of gestation and a high cortisolemia, shortly before birth, signals the initiation of parturition. In this experiment, all nine fetuses had a high cortisolemia (range=62 nmol/l to 461 nmol/l) when sera were collected. The normal serum cortisol levels in adult ewes range from 15 to 30 nmol/l (Rawlings, et al., *J Toxicol Environ. Health* (1998) 54:21–36). These observations support the conclusion that in utero-DNA vaccination had no adverse effects on fetal development.

Table 2 is a summary of data obtained from further safety studies. All fetuses immunized with plasmid DNA (n=19), protein vaccine (n=4), or exposed to PBS placebo (n=17) displayed normal fetal development and were born alive and without assistance. None of the ewes showed clinical signs of distress or illness following the surgical procedure. Plasmid DNA transfection and expression was confirmed by the presence of gD-specific serum antibody (ELISA, Western blot) and gD-specific LPR in 12/15 (80%) newborn lambs (Table 2). The number and frequency of blood leukocytes were compared between lambs exposed to various treatments in utero. There were no significant differences between treatment groups when values for blood mononuclear cells, polymorphonuclear cell or monocyte number were compared at birth and at 3 and 6 weeks of age (Table 3). Furthermore, in utero DNA immunization did not induce significant differences in the number of B lymphocytes, T lymphocytes, or activated T lymphocytes (CD25$^+$) present in blood at birth or 3 weeks of age (Table 4). Thus, oral exposure in utero to plasmid DNA did not appear to affect fetal gestation, neonatal viability, or significantly alter blood leukocyte populations.

EXAMPLE 2

Induction of an Immune Response by Fetal Nucleic Acid Immunization

In order to determine whether in utero, oral nucleic acid immunization was capable of producing an immune response, the following experiment was done. In particular, to investigate the induction of a gD-specific antibody response by tgD-plasmid immunization, all sera were analyzed with a gD-specific ELISA, described above in the methods. All DNA-vaccinated fetuses (4/4) responded to the single in utero-immunization with high titers of gD-specific serum antibodies (Table 1). In contrast, none of the PBS-injected fetuses had detectable levels of gD-specific serum antibodies. The fetus immunized with inactivated BHV-1 developed moderate gD-specific titers (Table 1). These observations confirmed that fetal lambs responded to a single DNA vaccination administered via the amniotic fluid.

The syndesmochorial placenta of sheep excludes maternal immunoglobulin from the fetal circulation (Hein, W. R., *The Immunologist* (1995) 3:12–18). However, to substantiate that the gD-specific antibodies were of fetal origin, sera from all ewes were also analyzed in the same ELISA. Maternal gD-specific antibodies were below the level of detection in all ewes whose fetuses were immunized with gD-plasmid. Thus, there was no evidence of antibody transmission from mother to fetus. These results also clearly demonstrate that there was no antibody transfer from the fetus to the mother.

EXAMPLE 3

Isotype-Switching and Neutralizing Activity

The hallmark of a functional immune system with cognate B cell-T cell interactions, is isotype-switching from IgM to IgG (Van-den-Eertwegh, et al., *J. Exp. Med.* (1993) 178:1555–1565; Allen, et al., *Science* (1993) 259:990–993). Monoclonal antibodies specific for bovine IgG1 were used to identify the isotype of the fetal gD-specific antibodies. High titers of gD-specific IgG1 were present only in sera from DNA-vaccinated fetuses (Table 1). To further evaluate the functional significance of the fetal antibody response, all sera were analyzed for virus neutralizing activity. Sera from all DNA-vaccinated fetuses contained moderate levels of BHV-1-neutralizing antibodies (Table 1). Furthermore, the level of neutralizing antibodies present in the sera of the DNA-vaccinated fetuses exceeded the virus neutralizing activity of the serum from the fetus immunized with inactivated BHV-1 (Table 1). As expected from the studies described above, viral neutralizing antibodies were not detected in sera from the PBS-injected fetuses or from the ewes carrying fetuses vaccinated with plasmid DNA.

EXAMPLE 4

Induction of Cellular Immune Responses in the Blood

Figure 1A:
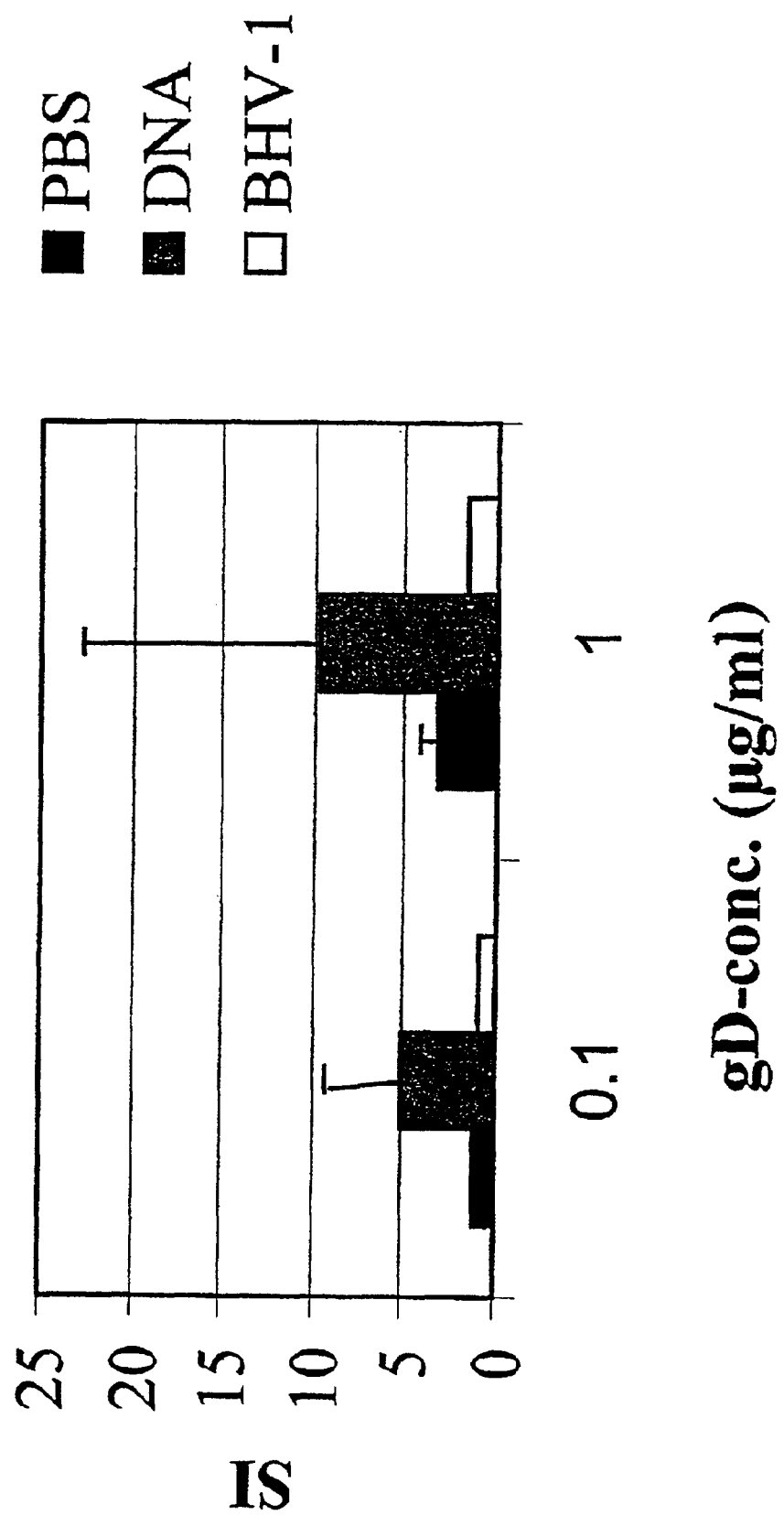
FIG. 1A shows the results of an experiment where PBMC from PBS (solid bar), tgD plasmid (grey bar), or irradiated BHV-1 (open bar) treated fetuses were stimulated with either 0.1 $\mu$g/ml or 1.0 $\mu$g/ml of recombinant BHV-1-tgD.

To analyze if nucleic acid immunization or fetuses orally in utero induced a cellular immune response, the following experiment was conducted. In particular, to determine if immunization with the tgD-encoding plasmid also induced a cell-mediated immune response, mononuclear cells were isolated on day 145 or 146 of gestation from fetal blood to assay gD-specific lymphoproliferative responses (LPR). Lymphocytes from all DNA-vaccinated fetuses proliferated in response to two different concentrations of recombinant gD-protein (0.1 $\mu$g/ml and 1.0 $\mu$g/ml; FIG. 1A). The average stimulation indices (SI) for the DNA immunized group were 5.2 (0.1 $\mu$g gD) and 9.7 (1.0 $\mu$g gD) respectively, whereas the PBS group had average SIs of 1.1 (0.1 $\mu$g gD) and 3.2 (1.0 $\mu$g gD). The inactivated BHV-1 immunized fetus had SIs of 1.0 (0.1 $\mu$g gD) and 1.7 (1.0 $\mu$g gD) respectively. Although, there was not a statistically significant difference between the LPR of DNA- and control-groups, this could be explained by the high LPR of DNA-vaccinated Fetus #7, which had stimulation indices (SI) of 9.8 (0.1 $\mu$g gD) and 24.2 (1.0 $\mu$g gD) respectively. High levels of serum cortisol can depress in vitro-lymphoproliferative responses (Auphan, et al., *Science* (1995) 270:286–290). Thus, the observed magnitude of the LPR of the DNA-immunized fetuses is even more remarkable and may present a minimal estimate of specific immune activation.

EXAMPLE 5

Figure 2:
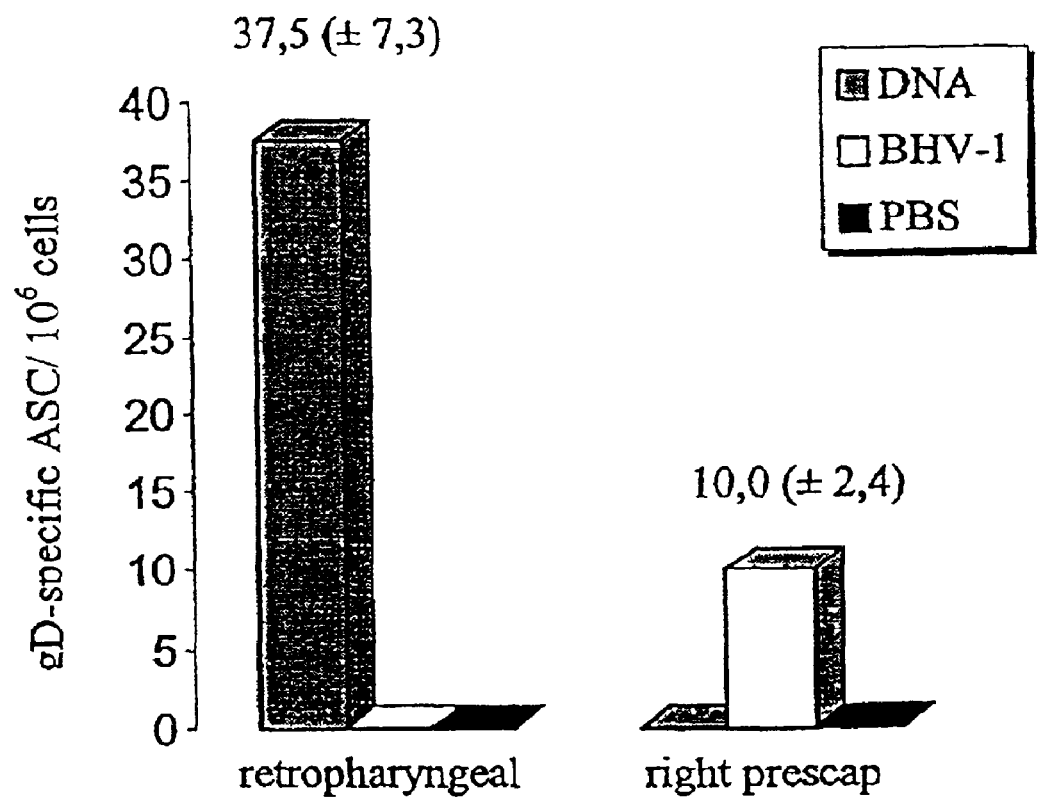
FIG. 2 shows detection of gD-specific antibody secreting cells (ASC) in the retropharyngeal and right prescapular lymph nodes. The number of gD-specific ASC was quantified by incubating $1 \times 10^6$ lymph node cells/well in triplicate wells that were either coated with tgD or PBS (negative control). Antigen-specific ASC were calculated by subtracting spots in control wells from spots in tgD-coated wells. Values represent the average of two (2/4) DNA vaccinated fetuses (#5 and #6, grey bar), the BHV-1-(open bar) and the PBS-treated fetuses (black bar).

Induction of a Local Immune Response by Nucleic Acid Immunization into the Oral Cavity An important factor for preventing neonatal diseases is the induction of effective mucosal immunity. In order to test for mucosal immunity, a variety of immune assays were used to analyze gD-specific immune responses of lymphocytes isolated from lymph nodes draining various mucosal sites. Two DNA-vaccinated fetuses had numerous gD-specific antibody secreting cells (ASC; ca. 40 gD-specific cells/million isolated cells) in the retropharyngeal lymph nodes, which drain the oral and nasal cavity (FIG. 2). In contrast, no gD-specific ASCs were detected in the retropharyngeal lymph nodes of the BHV-1 immunized and PBS-treated fetuses. No gD-specific ASC were detected in either the mediastinal (lung) or the mesenteric lymph nodes (intestine) of any of the fetuses (data not shown). As expected, low numbers of ASC were identified only in the right, but not the left, prescapular lymph node of the BHV-1 immunized fetus. The right prescapular lymph node drained the site of the subcutaneous BHV-1 injection (FIG. 2).

Figure 1B:
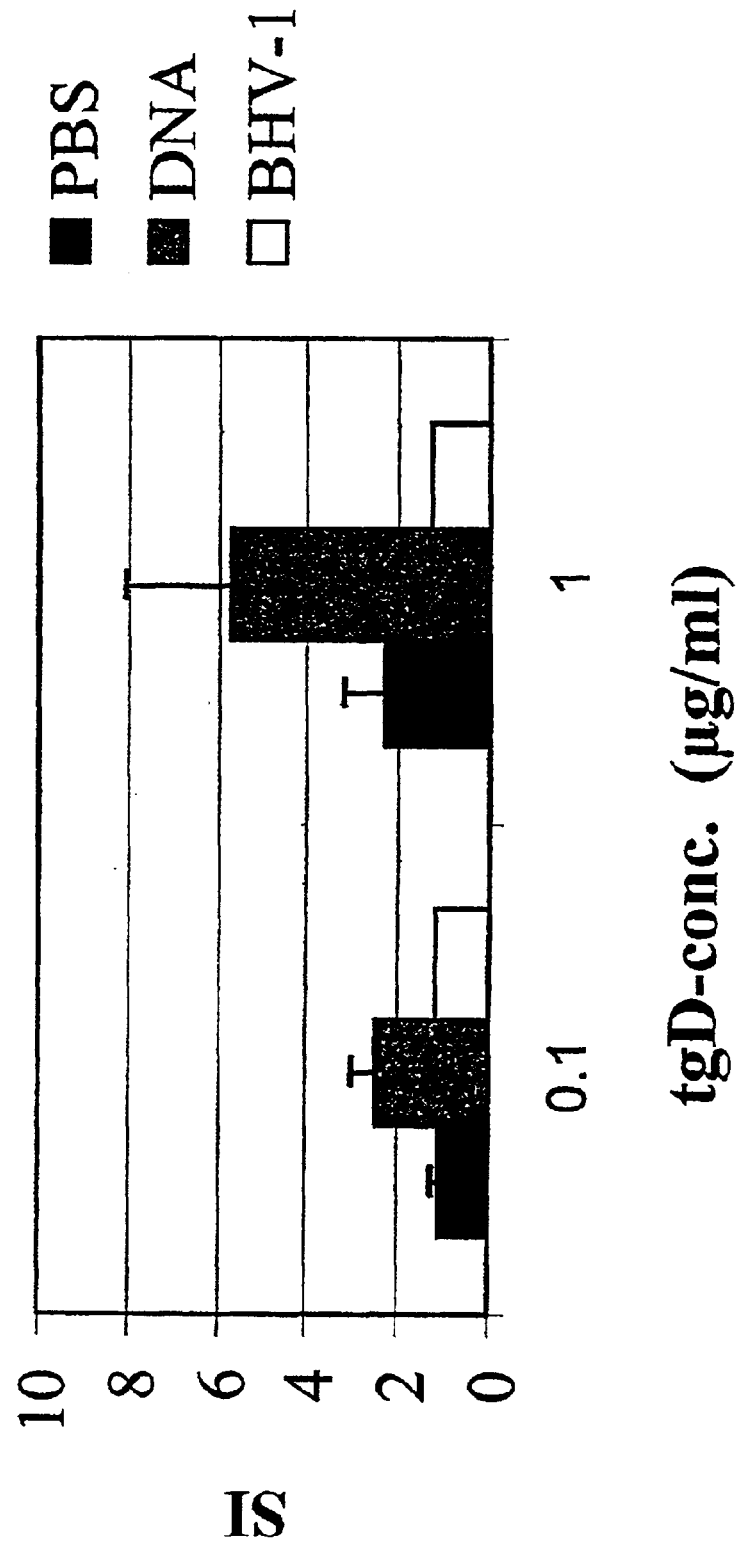
FIG. 1B shows the results of an experiment where lymphocytes were isolated from fetal retropharyngeal lymph nodes of the same fetuses and stimulated with 0.1 $\mu$g/ml or 1.0 $\mu$g/ml of tgD-protein. The values presented are the mean of triplicate wells and are expressed as mean stimulation index (SI) for each group of treated fetuses. Error bars are one standard deviation. A statistically significant difference ($p<0.005$, t-test) between treatment groups is indicated (*).

The LPR assay confirmed, that the retropharyngeal lymph node may represent the primary site of immune induction in DNA vaccinated fetuses (FIG. 1B). There was a statistically significant difference between the LPR of DNA-vaccinated fetuses when compared with the LPR of PBS-treated fetuses (p=0.015). No gD-specific proliferative responses were detected with cells isolated from the lymph nodes draining other mucosal sites. Taken together, the results from ASC- and LPR-assays clearly demonstrate that injecting gD-plasmid into the amniotic fluid in the fetal oral cavity induced a local immune response in the lymph node draining the site of injection.

EXAMPLE 6

Immune Response Following Boost at Birth

In order to determine whether the immune response achieved using in utero fetal immunization could be enhanced by a booster administration, the following study was conducted. Four groups of animals were used in this study. Groups I and II were immunized in utero with 500 $\mu$g tgD-encoding plasmid, as described above. Groups III and IV were immunized in utero with PBS (no plasmid DNA) as described above. Groups II and IV were subsequently boosted at birth with 500 $\mu$g tgD-encoding plasmid i.d. Blood was collected at 2 week intervals and serum IgG ELISA titers and PBMC were examined as measures of humoral and cellular immunity, respectively.

Figure 3:
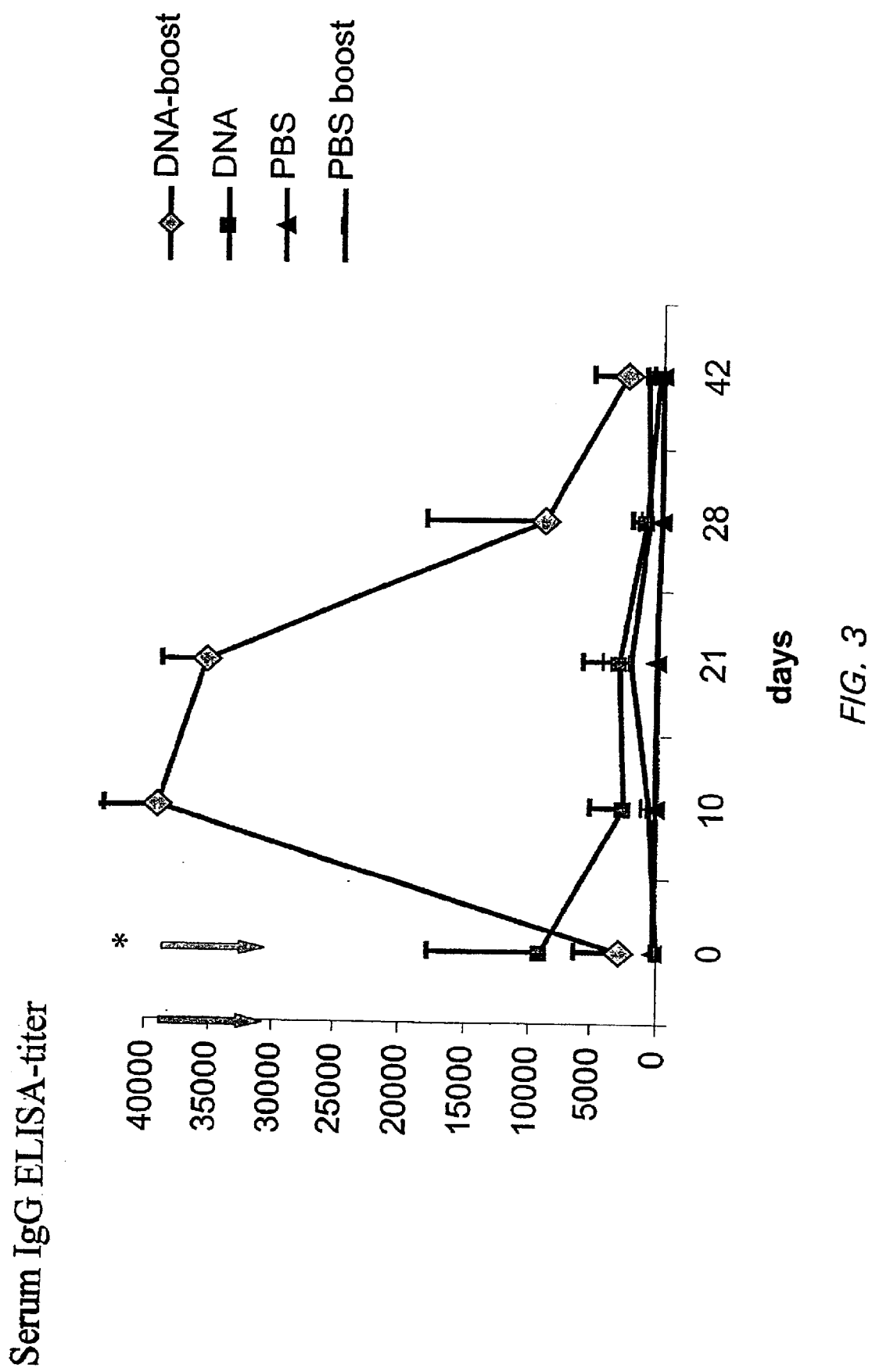
FIG. 3 shows serum IgG titers in blood samples from animals which had previously been immunized in utero with tgD (grey diamonds and black squares) or PBS (black triangles and black rectangles) and subsequently boosted at birth with tgD (grey diamonds and black rectangles), or not boosted (black squares and black diamonds). The arrows represent the times immunizations were administered.
Figure 4:
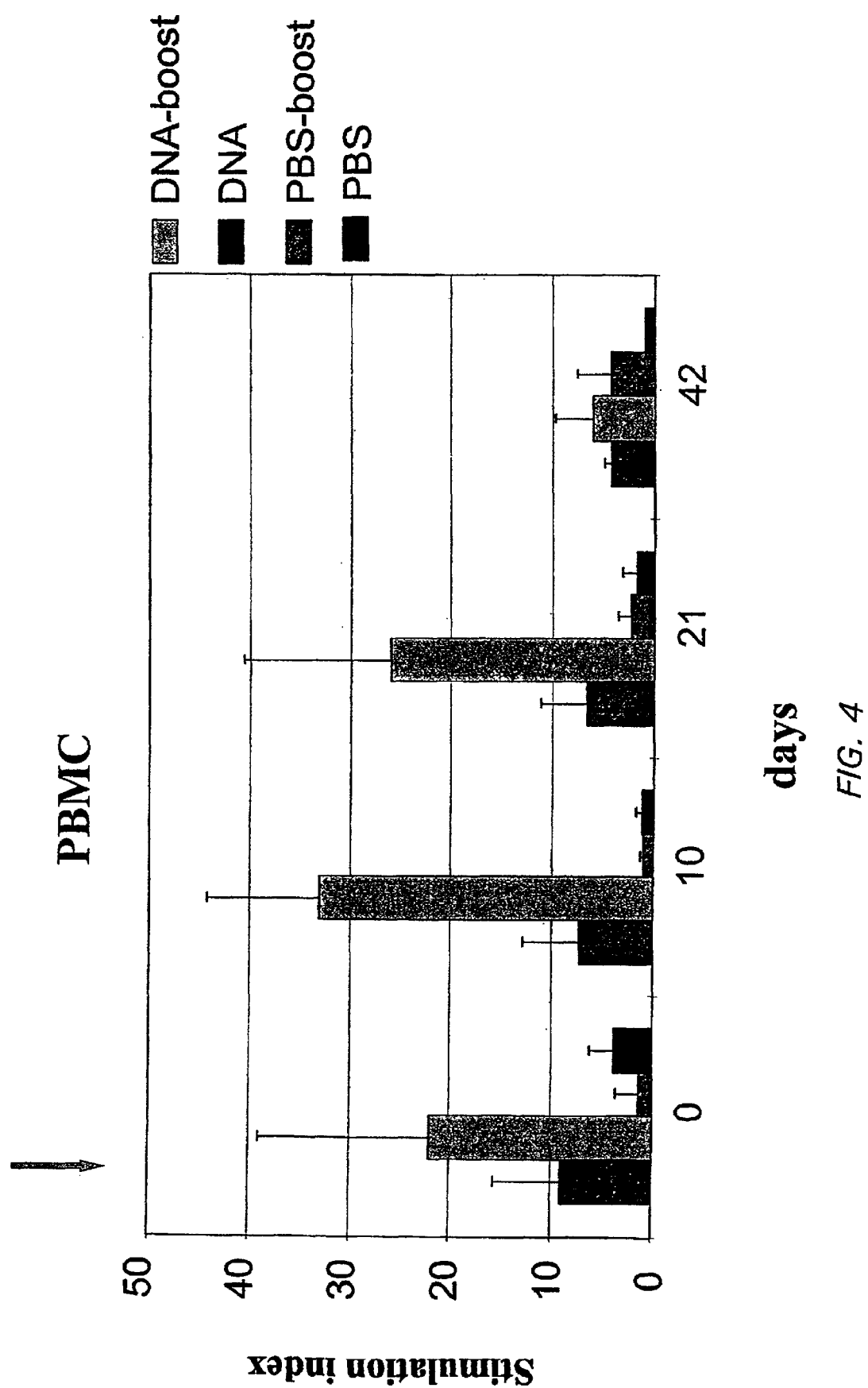
FIG. 4 shows lymphoproliferative responses of newborn blood mononuclear cells (PBMC) from tgD plasmid-boosted animals, as well as from animals which were not boosted.

As shown in FIGS. 3 and 4, booster immunization at birth significantly increased the magnitude of the induced immune response.

EXAMPLE 7

Induction of Long-Term Immune Memory in the Neonate

Figure 5:
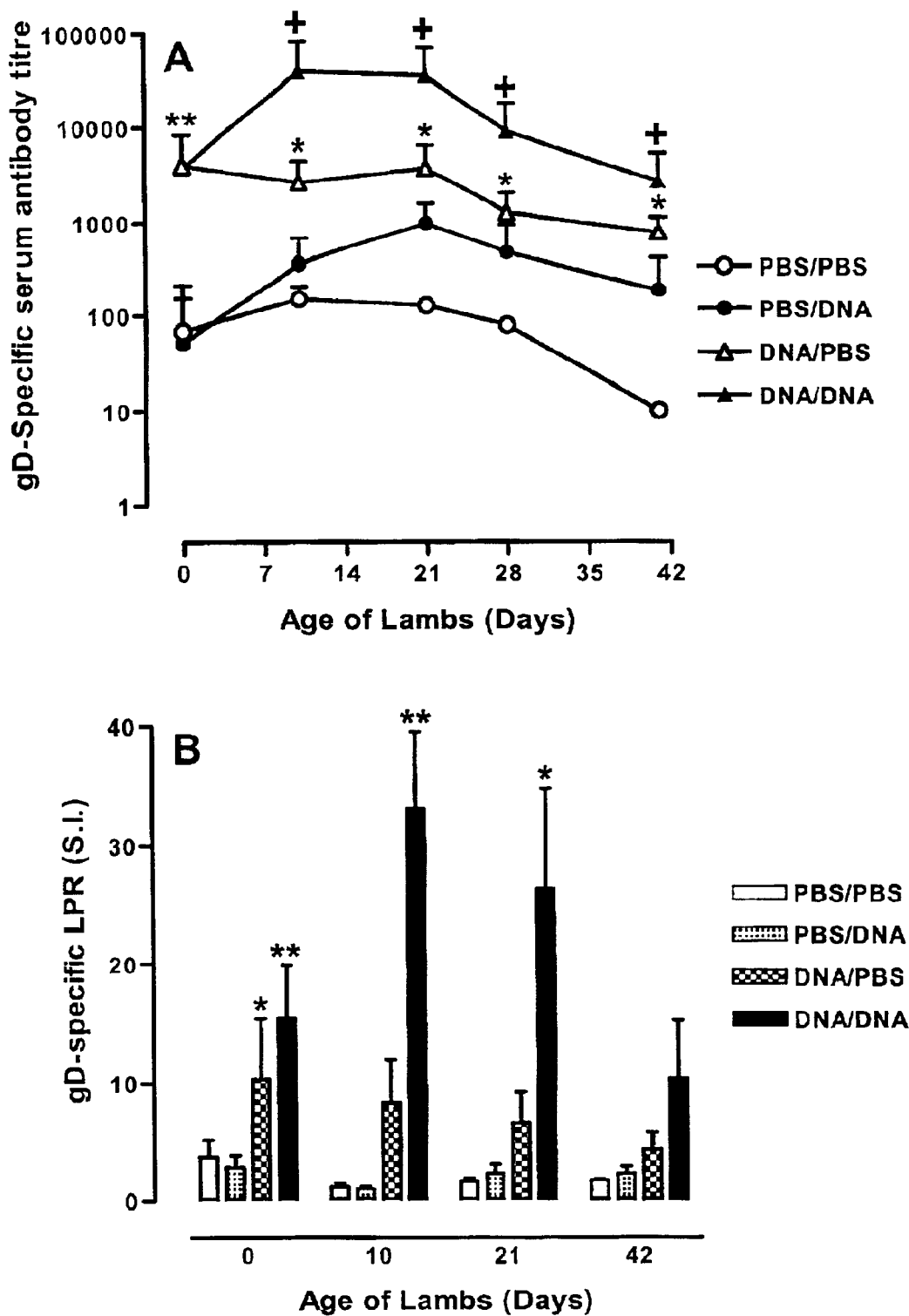
FIGS. 5A and 5B show the results of immune memory studies performed in neonatal lambs. Fetal lambs were orally immunized with either pSLIA-tgD (DNA; n=6) or PBS (PBS; n=6). Between 3–5 days of age, each treatment group was subdivided into two equal groups (n=3), that then received a secondary immunization with either PBS (DNA/PBS; PBS/PBS) or pSLIA-tgD (DNA/DNA; PBS/DNA).

An important concern regarding fetal immunization is the possible induction of immune tolerance, which would prevent the induction of specific immunity in the neonate. To analyze the induction of immune memory, fetal lambs were orally immunized with either 500 $\mu$g pSLIAtgD plasmid DNA (n=8) or PBS (n=7). Prior to suckling colostrum, 7 of 8 newborn lambs immunized in utero with pSLIAtgD had detectable gD-specific serum antibodies (Exp. I—Table 2; FIG. 5A). In contrast, none of the lambs immunized in utero with PBS had detectable gD-specific serum antibodies (Exp. I—Table 2; FIG. 5A). Subsequently at 3 days of age, three lambs from each group were injected intradermally, on the lateral aspect of the lower mandible, with 500 $\mu$g of pSLI-AtgD plasmid. Secondary DNA immunization of newborn lambs induced significantly (p<0.01) elevated gD-specific serum antibody titres relative to lambs that had received no in utero DNA immunization and newborn lambs that received a primary DNA immunization (FIG. 5A). In the absence of secondary DNA immunization at birth, lambs maintained significantly (p<0.05) elevated serum antibody titres for 6 weeks relative to naive lambs (PBS/PBS) but not relative to lambs that received a primary DNA immunization at birth. Thus, this data confirmed that in utero DNA immunization had induced gD-specific immune memory.

The anamnestic humoral immune response observed for gD was confirmed by assaying gD-specific proliferative responses of blood mononuclear cells (FIG. 5B). Seven of eight newborn lambs, immunized in utero with pSLIAtgD plasmid, displayed gD-specific LPR (S.I.>3.5) and these responses were significantly (p<0.05) different from naïve lambs. Furthermore, secondary DNA immunization at birth induced a significant (p<0.01) increase in gD-specific LPR relative to all other groups of lambs. Thus, both humoral and cellular gD-specific immune responses clearly indicated that in utero DNA immunization induced immune memory that responded strongly to secondary DNA immunization at birth. In addition, the primary response following fetal immunization (DNA/PBS) was significantly higher than that following neonatal immunization (PBS/DNA) (FIGS. 5A and 5B). Thus, in utero oral immunization was more effective than intradermal DNA vaccination in the neonate.

Figure 6:
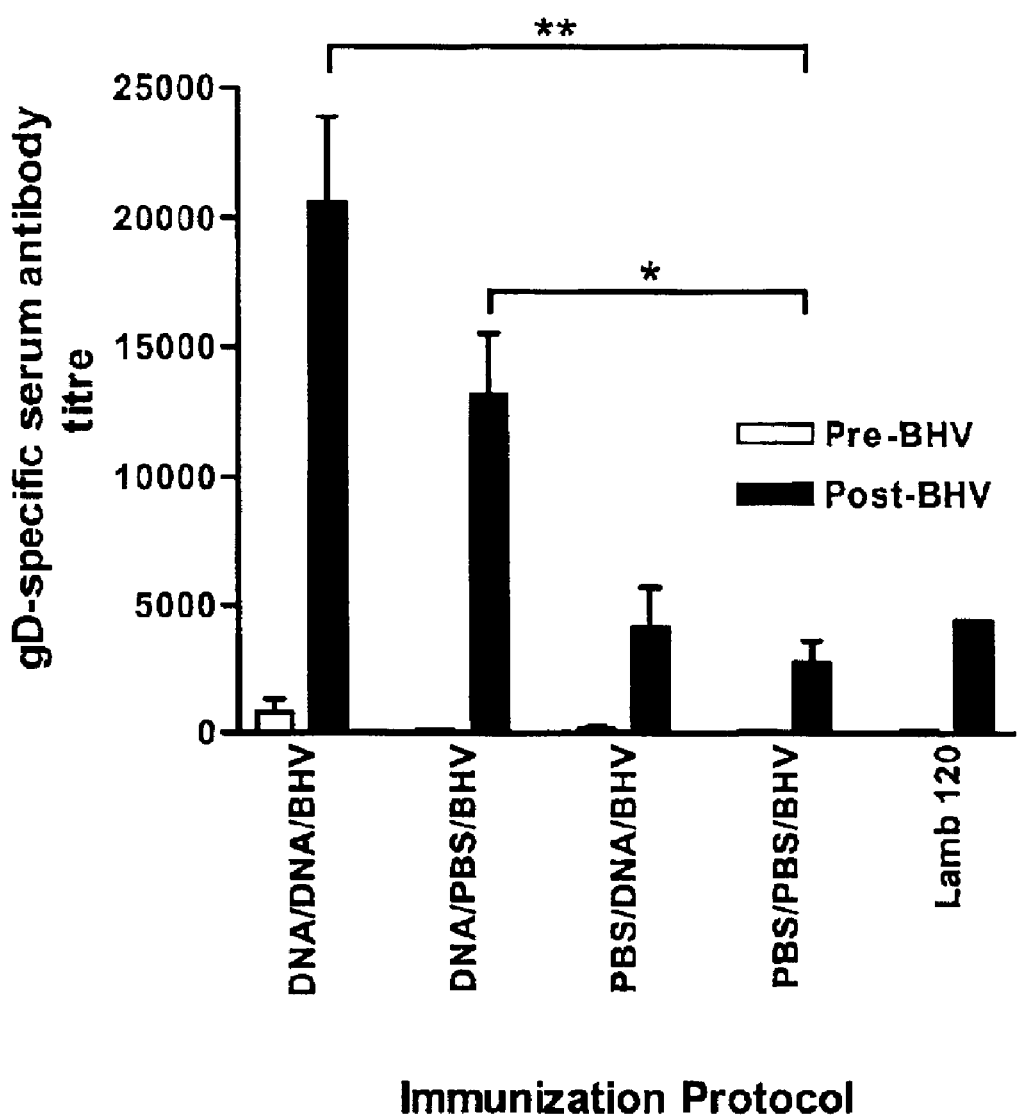
FIG. 6 shows antibody responses to inactivated BHV-1 vaccination. Sera from all lambs of the four treatment groups were analyzed in a gD-specific ELISA at 13 weeks of age (pre-BHV), prior to an intramuscular injection of inactivated BHV-1 vaccine (BHV), and at 15 weeks of age. Significant differences between DNA/DNA/BHV and PBS/PBS/BHV (**$p<0.01$) as well as between DNA/PBS/BHV and PBS/PBS/BHV-(*$p<0.05$) are indicated. Lamb 120 represents a lamb with no detectable response to in utero or neonatal DNA immunizations.

The one lamb with no detectable gD-specific response following in utero immunization (Exp. I—Table 2) could be explained by either a vaccine delivery failure or the induction of immune tolerance. To address this question, lambs at 13 weeks of age were further immunized with an inactivated BHV-1 vaccine. Within 2 weeks of BHV-1 vaccination, Lamb 120, a previous non-responder to in utero and neonatal DNA immunization, had a gD-specific antibody response as measured by both ELISA (FIG. 6) and western blot. The ELISA titre was within the same range as naïve lambs and lambs that had received a single intradermal DNA immunization at birth (FIG. 6—Lamb 120). Therefore, there was no evidence that either in utero or neonatal DNA immunization had induced gD-specific immune tolerance.

The duration of specific immune memory was determined following a single in utero immunization. At 13 weeks after birth, the majority of lambs had low titres of gD-specific antibody (FIG. 6) and lambs were then vaccinated with an inactivated BHV-1 vaccine. Following immunization, lambs that received a secondary DNA immunization at birth produced the highest gD-specific serum antibody titres and this response was significantly (p<0.01) greater than that of naïve lambs and approximately four-fold greater than that of lambs that received a primary DNA immunization at birth. Furthermore, lambs that received only a primary oral DNA exposure in utero also had significantly (p<0.05) elevated antibody titres when compared to naïve lambs and approximately a three-fold greater response than that of lambs that received a primary DNA immunization at birth (FIG. 6). There was no significant difference when gD-specific antibody titres were compared between lambs receiving a single in utero immunization and lambs that received a secondary DNA immunization at birth. Therefore, data were pooled for these two groups (n=6) and compared (t test) with the responses of lambs that received a single DNA immunization at birth (n=4). This analysis revealed a highly significant (p<0.005) difference between these two groups and further supported the previous conclusion that in utero immunization induced immune memory more effectively than did neonatal immunization. The present data also demonstrate that a single in utero exposure to plasmid DNA could induce immune memory that persisted for at least 3 months after birth.

EXAMPLE 8

Induction of Mucosal Immunity and Reduction of Viral Infection

Figure 7:
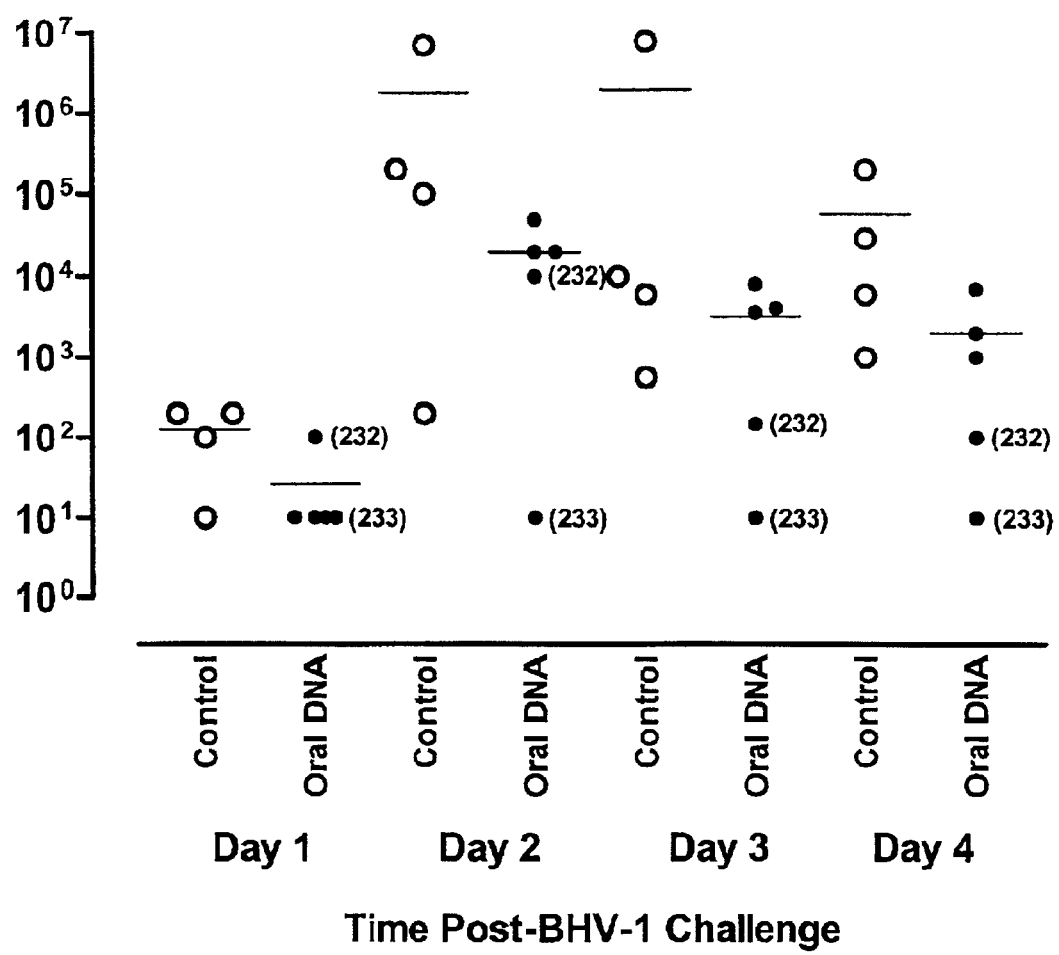
FIG. 7 shows virus shedding in nasal secretions following BHV-1 challenge of newborn lambs. Fetal lambs were orally immunized in utero with either 500 $\mu$g pSLIAtgD plasmid (DNA; n=5) or PBS (PBS; n=4). Between 7–10 days of age, newborn lambs were aerosol-challenged with $5-7 \times 10^7$ infectious particles of BHV-1 strain 108 and virus shedding in nasal secretions was assayed in vitro with a plaque assay. Data presented are values for individual lambs for the first four days p.i. and group means are indicated by the horizontal bar.

In order to analyze mucosal immune responses in newborn lambs before and after BHV-1 challenge, the following experiment was conducted. Seven fetuses were orally immunized with 500 µg of plasmid pSLIAtgD and four were injected orally with PBS (Exp. II—Table 2). At 7–10 days of age, these lambs were challenged with BHV-1 strain 108 and FIG. 7 summarizes viral shedding data for the five of seven lambs that responded to in utero DNA immunization. Lambs immunized in utero with DNA shed, on average, one to two logs less infectious virus during the first four days p.i. In fact, two lambs (#232 and 233; FIG. 7) shed very little infectious virus at any time following challenge. Thus, in utero DNA vaccination induced immune responses that could limit viral replication at the site of primary infection.

To identify the immune responses responsible for reduced viral shedding, the systemic and mucosal immune responses were analyzed before and after viral challenge. Lambs injected orally with PBS in utero had no detectable gD-specific immune responses prior to viral infection and did not develop significant increases in gD-specific serum antibody titre (FIG. 8A), secretory (S)IgA titre (FIG. 8B), and gD-specific LPR (FIG. 8C) by day 12 p.i. In contrast, lambs immunized in utero with DNA had detectable gD-specific serum antibody titres (FIG. 8A), SIgA titres (FIG. 8B), and LPR (FIG. 8C) prior to viral infection and there was a significant increase in gD-specific serum antibody titres (FIG. 8A) and LPR (FIG. 8C) p.i. Thus, fetal immunization induced both systemic and mucosal immune responses and immune memory that responded to viral infection. Furthermore, both lambs that lacked a detectable response to in utero DNA immunization (Table 2-Exp. II) did develop gB- and gD-specific serum antibodies following viral infection. The gD-specific antibody response in these lambs provided further evidence that in utero DNA immunization did not induce immune tolerance.

To further clarify the role of systemic and mucosal immune responses in preventing and clearing viral infection, immune responses of lambs (FIG. 7: #232 and 233) which shed the least virus after infection were compared. Prior to challenge, Lamb #233 had high gD-specific IgG serum antibody (titre=6089), gD-specific LPR (SI=60), and SIgA in nasal secretions (titer=2750) but on day 12 p.i. SIgA (titre=230) and LPR (SI=42.3) had decreased. The gD-specific serum antibody titre did increase (titre=24460) but the absence of gB-specific antibodies p.i. was an indication of sterile immunity. In contrast, prior to infection, lamb #232 had low gD-specific serum antibody (titre=383), SIgA (titer<10) and LPR (SI=4.6) but a marked increase in gD-specific LPR (S.I.=63.1) p.i. Furthermore, at day 12 p.i. there was a relatively small increase in gD-specific serum antibody (titre=1312) and detectable gB-specific serum antibody which suggests that viral clearance was mediated primarily by a cell-mediated immune response. Collectively, this analysis of immune responses indicates that in utero DNA immunization induced both systemic and mucosal immune responses and both types of immunity may contribute to disease protection.

EXAMPLE 9

Oral Immunization in utero with HBsAg

To test the broader validity of oral DNA immunization in utero, the efficacy of another plasmid vector and vaccine antigen was assessed. HBsAg was selected since HBV is an important human pathogen that is vertically transmitted from mother to newborn infant. Furthermore, the efficacy of oral DNA vaccination in utero could be compared with that of the recombinant protein, as there exists known correlation between serum antibody titre (>10 mIU/ml) and disease protection.

Four fetuses were orally immunized with 500 µg pMCG-16 plasmid encoding HBsAg and four fetuses were injected intramuscularly with 10 µg recombinant, purified HBsAg formulated in alum, (Engerix-B™), the recommended dose for newborn infants. Seven fetuses were injected orally with PBS, to serve as negative controls for HB ELISA specificity, and none of these lambs developed detectable HBsAg antibody titres throughout the experimental period. All newborn lambs were seronegative for HBsAg but at three weeks of age, three of the four lambs (75%) orally immunized with pMCG-16 plasmid had protective antibody titres but only one of four lambs (25%) injected in utero with Engerix-B™ vaccine developed a protective antibody titre (FIG. 9). The marked difference in protective antibody titres between DNA and protein immunized groups persisted for at least the next 8 weeks. Thus, a single oral DNA vaccination of fetuses induced more rapid seroconversion and a higher frequency of disease protection in neonates than a single in utero vaccination with recombinant protein vaccine.

The above studies confirm that fetal lambs, in the last trimester of gestation, are not only immunocompetent but also respond exceptionally well to oral DNA vaccination. This is surprising since previous investigations indicated that oral vaccination was less efficacious than other routes of DNA immunization (Sha, et al., *Immunobiol.* (1999) 200:21; Roy, et al., *Nat. Med.* (1999) 5:387; Etchard, et al., *J. Gen. Virol.* (1997) 78:1577; McCluskie and Davis, *Crit. Rev. Immunol.* (1999) 19:303–329; Rankin, et al., *Europ. Soc. of Virol. Conference* (September 2000), Italy). The strong response of fetal lambs to oral DNA vaccination, however, suggests that some unique aspect of fetal physiology might enhance DNA transfection or gene expression. Without being bound by a particular theory, one possible explanation for the enhanced efficacy of oral immunization in utero might be the much lower turnover rate for mucosal epithelial cells in the fetus (Moon and Joel, *Am. J. Vet. Res.* (1975) 36:187). A reduced rate of epithelial cell attrition could prolong the duration of plasmid expression and thereby increase antigenic exposure in the fetus. Thus, induction of immune memory in utero could be greatly enhanced by using a DNA vaccine that facilitates antigen expression over an extended interval (reviewed in Gurunathan, et al., *Ann. Rev. Immunol.* (2000) 18:927).

The developmental state of the fetal immune system might also contribute to a more efficient induction or immune memory. A large pool of naive re-circulating T cells, with a diverse TcR repertoire, is present in the fetal lamb (Cunningham, et al., *Vet. Immunol. Immunopathol.* (1999) 72:175). These fetal T cells have a relatively long life-span when compared to T cells in the neonate. Thus, differences in fetal lymphocyte physiology might also contribute to increased memory T cell survival following antigen stimulation. The very high gD-specific LPR, observed following secondary immunization of newborn lambs (FIG. 5B), confirmed that memory T cells induced in utero can survive the functional transition that occurs in the immune system following birth (Cunningham, et al., *Vet. Immunol. Immunopathol.* (1999) 72:175). Furthermore, immune memory induced in utero persisted for at least 3 months after birth, even in the absence of a secondary antigenic stimulation (FIG. 6). This is the first report to confirm that memory T cells, induced during fetal development, survive and function in the neonate. Thus, the present animal model provides a unique opportunity to further define the functional differences between naive and memory T cells.

In conclusion, the above results demonstrate, for the first time, that a single in utero immunization with plasmid-DNA effectively induces both mucosal and systemic immune responses in fetal lambs. Moreover, the immune response can be boosted at birth to increase the magnitude of the initial response. Thus, fetal DNA vaccination, with or without a subsequent boost, provides a safe and effective method for preventing or reducing the high risk of vertical disease transmission during pregnancy and following birth. Vaccination may be performed using surgical techniques such as amniocentesis, which involves minimal surgical invasion. The present observations have significant application for developing new gene therapy strategies to target the upper and lower respiratory tract. The present techniques may also be used for targeting gene expression to various mucosal sites where transient expression of a plasmid DNA may be of significant value.

TABLE 1 gD-specific antibody response in fetal sera

| Fetus | Immunogen | Total gD-specific antibody titre* | gD-specific IgG1 antibody titre[+] | Neutralizing antibody titre |
|---|---|---|---|---|
| 1 | PBS | 11 ± 15 | nd[++] | <2 |
| 2 | PBS | 14 ± 20 | nd | <2 |
| 3 | PBS | 10 ± 14 | nd | <2 |
| 4 | PBS | 11 ± 16 | nd | <2 |
| 5 | tgD-plasmid | 2047 ± 253 | 1586 ± 120 | 32 |
| 6 | tgD-plasmid | 5034 ± 333 | 3864 ± 233 | 64 |
| 7 | tgD-plasmid | 2628 ± 258 | 4948 ± 799 | 32 |
| 8 | tgD-plasmid | 1146 ± 672 | 412 ± 267 | 8 |
| 9 | irr. BHV-1 | 666 ± 125 | 1202 ± 334 | <2 |

*Rabbit anti-sheep IgG (H + L chain-specific)
[+]BIg715A monoclonal antibody
[++]not detected

TABLE 2

Immune responses of newborn lambs to in utero oral DNA vaccination

| Experiment[a] | In Utero Immunization[b] | Vaccine Response in Neonates[c] | Serum Antibody Titre[d] |
|---|---|---|---|
| I | pSLIA-tgD | 7/8 | 5589 ± 3650 |
|   | PBS | 0/7 | 112 ± 57 |
| II | pSLIA-tgD | 5/7 | 1083 ± 352.4 |
|    | PBS | 0/4 | 168 ± 143 |
| III | pMCG-16-HBsAg | 3/4 | 95.6 ± 68.9 |

TABLE 2-continued

Immune responses of newborn lambs to in utero oral DNA vaccination

| Experiment[a] | In Utero Immunization[b] | Vaccine Response in Neonates[c] | Serum Antibody Titre[d] |
|---|---|---|---|
| | Engerix-B ™ | 1/4 | 66.1 ± 64.3 |
| | PBS | 0/6 | 0 |

[a]Each experiment was performed independently
[b]Fetal lambs were immunized on days 121–123 of gestation (148 day gestation) by injecting the DNA vaccine or PBS into the oral cavity. Engerix-B* vaccine was injected intramuscularly.
[c]gD-specific serum antibody responses were assayed during the first week after birth and were defined as the highest reciprocal of the serum dilution that gave an OD reading two-fold greater than the average values for sera from naïve fetuses. Protective HB serum antibody titres were defined as >10 mIU/ml and were determined at 3 weeks of age.
[d]Data presented are the mean ± standard error of the mean for values from responding animals and the range of values are presented in parenthesis.

TABLE 3

Effect of in utero DNA immunisation on blood leukocyte populations of newborn lambs

| | Number of cells (×10$^6$)/ml of blood[a] | | | | | |
|---|---|---|---|---|---|---|
| Leukocyte | 2–5 Days[b] | | 3 Weeks[b] | | 6 Weeks[b] | |
| Population | PBS[c] | DNA[d] | PBS[c] | DNA[d] | PBS[c] | DNA[d] |
| Total WBC[e] (×10$^6$/ml) | 5.4 ± 1.9[f] | 4.6 ± 1.9 | 5.7 ± 1.1 | 5.7 ± 1.1 | 8.1 ± 1.9 | 6.6 ± 0.4 |
| Lymphocytes (×10$^6$/ml) | 1.2 ± 0.5 | 2.0 ± 1.5 | 3.2 ± 0.9 | 2.5 ± 0.6 | 4.1 ± 0.2 | 3.2 ± 0.9 |
| PMN[g] (×10$^6$/ml) | 3.9 ± 1.7 | 2.3 ± 0.7 | 2.2 ± 0.3 | 2.7 ± 1.1 | 3.8 ± 2.0 | 3.2 ± 1.5 |
| Monocytes (×10$^6$/ml) | 0.2 ± 0.2 | 0.3 ± 0.2 | 0.2 ± 0.1 | 0.2 ± 0.1 | 0.2 ± 0.1 | 0.1 ± 0.05 |

[a]Cell number/ml of blood was calculated by multiplying total leukocyte number (WBC)/ml of blood by the percentage of cells in each lineage, as determined by differential count of 100 cells on Giemsa stained blood smears.
[b]Average age of lambs when the analyses of blood leukocyte numbers were performed.
[c]Fetal lambs (n = 4) injected orally with 5 ml pyrogen-free PBS on days 122–124 gestation.
[d]Fetal lambs (n = 4) injected orally with 500 μg pSLIA-tgD plasmid in 5 ml pyrogen-free PBS on days 122–124 gestation and having gD-specific serum antibodies at birth.
[e]The total number of leukocytes/ml of blood was determined with a Cell-Dyn 3500 R Analyzer
[f]Data presented are the mean ± one standard deviation of values from each group.
[g]Polymorphonuclear cells (PMN) included neutrophils, eosinophils, and basophils

TABLE 4

Phenotype analysis of lymphocyte populations in the blood of newborn lambs

| | Number of cells (×10$^6$)/ml of blood[a] | | | |
|---|---|---|---|---|
| Cell | 2–5 Days[b] | | 3 Weeks[b] | |
| Phenotype | PBS[c] | DNA[d] | PBS[c] | DNA[d] |
| PBMC | 1.4 ± 0.4[e] | 1.7 ± 0.8 | 3.5 ± 0.9 | 3.5 ± 0.8 |
| sIgM$^+$ B cells | 0.05 ± 0.04 | 0.05 ± 0.04 | 0.15 ± 0.03 | 0.19 ± 0.08 |
| sIgG1$^+$ B cells | 0.03 ± 0.02 | 0.08 ± 0.06 | 0.05 ± 0.03 | 0.09 ± 0.03 |
| CD5$^+$ T cells | 0.9 ± 0.3 | 1.1 ± 0.5 | 1.9 ± 0.5 | 1.8 ± 0.7 |
| CD4$^+$ T cells | 0.3 ± 0.1 | 0.3 ± 0.2 | 0.6 ± 0.3 | 0.6 ± 0.2 |
| CD8$^+$ T cells | 0.13 ± 0.09 | 0.15 ± 0.06 | 0.5 ± 0.2 | 0.4 ± 0.1 |
| γδ TcR$^+$ T cells | 0.3 ± 0.2 | 0.3 ± 0.15 | 0.9 ± 0.4 | 0.7 ± 0.3 |
| CD25$^+$ CD5$^+$ T cells | 0.07 ± 0.03 | 0.10 ± 0.05 | 0.25 ± 0.05 | 0.21 ± 0.02 |

[a]Cell number/ml of blood was calculated by multiplying the number of blood mononuclear cells (PBMC)/ml of blood, as determined by CBC, by the percentage of cells expressing a specific lineage marker, as determined by flow cytometry.
[b]Phenotypic analyses and CBC were performed on the same day for lambs between 2–5 days of age and when lambs were on average 3 weeks of age.
[c]Fetal lambs (n = 4) injected orally with 5 ml pyrogen-free PBS on days 122–124 gestation.
[d]Fetal lambs (n = 4) injected orally with 500 μg pSLIA-tgD plasmid in 5 ml pyrogen-free PBS on days 122–124 gestation and having gD-specific serum antibodies at birth.
[e]Data presented are the mean ± one standard deviation of values from each group.

Although preferred embodiments of the subject invention have been described in some detail, it is understood that obvious variations can be made without departing from the spirit and the scope of the invention as defined by the appended claims.

What is claimed is:

1. A method of eliciting mucosal immunity in a mammalian subject, said method comprising administering a first vaccine composition to a fetal mammalian subject in utero during the third trimester of pregnancy, directly to a mucosal membrane or directly into the mouth of the subject, said first vaccine composition comprising a non-viral recombinant vector that transforms cells of the subject, wherein said recombinant vector comprises a nucleic acid molecule encoding a selected antigen operably linked to control elements capable of effecting the expression of said nucleic acid molecule in vivo, whereby said nucleic acid molecule is expressed by the transformed cells at a level sufficient to induce immunity to said antigen in the subject.

2. The method of claim 1, wherein the said antigen is a viral antigen.

3. The method of claim 2, wherein said viral antigen is a herpesvirus antigen.

4. The method of claim 2, wherein said viral antigen is a hepatitis virus antigen.

5. The method of claim 1, wherein said administration is directly into the mouth of said subject.

6. The method of claim 1, further comprising administering a second vaccine composition to the mammalian subject at birth to boost the immune response to the antigen encoded by the nucleic acid molecule in the first vaccine composition.

7. The method of claim 6, wherein the second vaccine composition comprises the recombinant vector present in the first vaccine composition.

8. The method of claim 6, wherein the second vaccine composition is a subunit vaccine composition that comprises the antigen encoded by the nucleic acid molecule present in the first vaccine composition.

9. The method of claim 1, wherein the non-viral recombinant vector is a recombinant plasmid.

10. A method of eliciting an a protective immune response in a mammalian subject, said method comprising:

(a) administering a first vaccine composition directly to a mucosal membrane or directly into the mouth of a mammalian fetal subject in utero during the third trimester of pregnancy, said first vaccine composition comprising a recombinant plasmid that transforms cells of the subject wherein said recombinant plasmid comprises a DNA sequence encoding a selected viral antigen operably linked to control elements capable of effecting the expression of said coding sequence in vivo, whereby said coding sequence is expressed by the transformed cells at a level sufficient to elicit a protective immune response to said antigen in the subject; and (b) administering a second vaccine composition to the mammalian subject at birth to boost the immune response to the antigen encoded by the recombinant vector in the first vaccine composition.

11. The method of claim 10, wherein the second vaccine composition comprises the recombinant vector present in the first vaccine composition.

12. The method of claim 10, wherein the second vaccine composition is a subunit vaccine composition that comprises the antigen encoded by the recombinant vector present in the first vaccine composition.

\* \* \* \* \*